United States Patent
Gordon et al.

(10) Patent No.: US 9,211,147 B2
(45) Date of Patent: Dec. 15, 2015

(54) SPINOUS PROCESS FUSION IMPLANTS

(75) Inventors: Charles Gordon, Tyler, TX (US);
Daniel Triplett, Providence, UT (US);
Darin Ewer, Providence, UT (US);
Nathan Nelson, Hyde Park, UT (US);
M. Mary Sinnott, Logan, UT (US);
Andrew Fauth, River Heights, UT (US);
Marc Yap, The Colony, TX (US)

(73) Assignee: OsteoMed LLC, Addison, TX (US)

( * ) Notice: Subject to any disclaimer, the term of this patent is extended or adjusted under 35 U.S.C. 154(b) by 382 days.

(21) Appl. No.: 12/853,689

(22) Filed: Aug. 10, 2010

(65) Prior Publication Data
US 2011/0022090 A1    Jan. 27, 2011

Related U.S. Application Data

(63) Continuation-in-part of application No. 12/820,575, filed on Jun. 22, 2010.

(60) Provisional application No. 61/219,687, filed on Jun. 23, 2009, provisional application No. 61/232,692, filed on Aug. 10, 2009, provisional application No. 61/366,755, filed on Jul. 22, 2010.

(51) Int. Cl.
*A61B 17/70* (2006.01)

(52) U.S. Cl.
CPC .................................. *A61B 17/7068* (2013.01)

(58) Field of Classification Search
CPC ........... A61B 17/7062–17/7071; A61F 2/4405
USPC ........... 606/60, 246–269, 272–273, 278–279, 606/70–71, 282, 286–291
See application file for complete search history.

(56) References Cited

U.S. PATENT DOCUMENTS

| | | |
|---|---|---|
| 3,242,922 A | 3/1966 | Thomas |
| 3,469,573 A | 9/1969 | Florio |

(Continued)

FOREIGN PATENT DOCUMENTS

| | | |
|---|---|---|
| EP | 1477124 B1 | 10/2007 |
| JP | 2004-535239 A | 11/2004 |

(Continued)

OTHER PUBLICATIONS

Office Action issued for Japanese Potent Application No. 2012-189058, dated Jun. 3, 2014, 6 pages with English language translation.

(Continued)

*Primary Examiner* — Eduardo C Robert
*Assistant Examiner* — Michelle C Eckman
(74) *Attorney, Agent, or Firm* — Norton Rose Fulbright US LLP

(57) ABSTRACT

A bone plate assembly including at least one bone plate, polyaxially adjustable fixation elements and a polyaxially adjustable locking mechanism. A first plate includes at least one polyaxial element for lockable connection with a fixation pad, and a connection feature which allows the plate to translate and polyaxially rotate relative to the locking mechanism. A second plate includes at least one polyaxial element for connection with a fixation pad and a connection feature for non-rotatable connection with the locking mechanism. The locking mechanism allows translation and polyaxial adjustment of the first plate relative to the second plate and locks the first and second plates via a taper lock. The fixation pad includes a deflectable spacer configured to prevent premature locking of the pad. Methods for implantation of the bone plate assembly between two bone structures are disclosed. Instrumentation for implantation, compression and locking of the bone plate assembly is disclosed.

32 Claims, 18 Drawing Sheets

(56) References Cited

U.S. PATENT DOCUMENTS

| | | | |
|---|---|---|---|
| 3,648,691 A | 3/1972 | Lumb et al. | |
| 4,066,082 A | 1/1978 | Arcan et al. | |
| 4,290,328 A | 9/1981 | Clark | |
| D281,814 S | 12/1985 | Pratt et al. | |
| 4,570,623 A | 2/1986 | Ellison et al. | |
| 4,592,346 A | 6/1986 | Jurgutis | |
| 4,848,328 A | 7/1989 | Laboureau et al. | |
| 4,852,558 A | 8/1989 | Outerbride | |
| 4,913,144 A | 4/1990 | Del Medico | |
| 4,994,073 A | 2/1991 | Green | |
| 5,007,909 A | 4/1991 | Rogozinski | |
| 5,011,484 A | 4/1991 | Beard | |
| 5,053,038 A | 10/1991 | Sheehan | |
| 5,074,864 A | 12/1991 | Cozad et al. | |
| 5,108,422 A | 4/1992 | Green et al. | |
| 5,196,318 A | 3/1993 | Baldwin et al. | |
| 5,201,746 A | 4/1993 | Shichman | |
| 5,246,442 A | 9/1993 | Ashman et al. | |
| 5,261,909 A | 11/1993 | Sutterlin et al. | |
| 5,290,312 A | 3/1994 | Kojimoto et al. | |
| 5,395,370 A | 3/1995 | Muller et al. | |
| 5,454,814 A | 10/1995 | Comte | |
| 5,496,318 A | 3/1996 | Howland et al. | |
| 5,609,634 A | 3/1997 | Voydeville | |
| 5,611,800 A | 3/1997 | Davis et al. | |
| 5,626,592 A | 5/1997 | Phillips et al. | |
| 5,645,599 A | 7/1997 | Samani | |
| 5,713,911 A | 2/1998 | Racenet et al. | |
| 5,722,976 A * | 3/1998 | Brown | 606/281 |
| 5,836,948 A | 11/1998 | Zucherman et al. | |
| 5,853,414 A | 12/1998 | Groiso | |
| 5,893,889 A | 4/1999 | Harrington | |
| 5,941,881 A | 8/1999 | Barnes | |
| 6,007,538 A | 12/1999 | Levin | |
| 6,148,696 A | 11/2000 | Chiang | |
| 6,238,397 B1 | 5/2001 | Zucherman et al. | |
| 6,312,431 B1 | 11/2001 | Asfora | |
| 6,332,883 B1 | 12/2001 | Zucherman et al. | |
| 6,336,928 B1 | 1/2002 | Guerin et al. | |
| 6,352,537 B1 | 3/2002 | Strnad | |
| 6,364,883 B1 | 4/2002 | Santilli | |
| 6,375,683 B1 | 4/2002 | Crozet et al. | |
| 6,379,355 B1 | 4/2002 | Zucherman et al. | |
| 6,440,169 B1 | 8/2002 | Elberg et al. | |
| 6,443,987 B1 | 9/2002 | Bryan | |
| 6,451,019 B1 | 9/2002 | Zucherman et al. | |
| 6,485,518 B1 | 11/2002 | Cornwall et al. | |
| 6,558,387 B2 | 5/2003 | Errico et al. | |
| 6,565,573 B1 | 5/2003 | Ferrante et al. | |
| 6,582,435 B2 | 6/2003 | Wellisz et al. | |
| 6,641,585 B2 | 11/2003 | Sato et al. | |
| 6,695,842 B2 | 2/2004 | Zucherman et al. | |
| 6,699,247 B2 | 3/2004 | Zucherman et al. | |
| 6,712,819 B2 | 3/2004 | Zucherman et al. | |
| 6,761,720 B1 | 7/2004 | Senegas | |
| 6,783,531 B2 | 8/2004 | Allen | |
| 6,796,983 B1 | 9/2004 | Zucherman et al. | |
| 6,923,812 B1 | 8/2005 | Wellisz | |
| 6,969,391 B1 | 11/2005 | Gazzani | |
| 7,025,787 B2 | 4/2006 | Bryan et al. | |
| 7,048,736 B2 * | 5/2006 | Robinson et al. | 606/86 B |
| 7,060,068 B2 | 6/2006 | Tromanhauser et al. | |
| 7,229,444 B2 | 6/2007 | Boyd | |
| 7,250,060 B2 | 7/2007 | Trieu | |
| 7,255,698 B2 | 8/2007 | Michelson | |
| 7,294,128 B2 | 11/2007 | Alleyne et al. | |
| 7,335,203 B2 * | 2/2008 | Winslow et al. | 606/249 |
| 7,377,921 B2 | 5/2008 | Studer et al. | |
| 7,393,361 B2 | 7/2008 | Zubok et al. | |
| 7,396,360 B2 | 7/2008 | Lieberman | |
| 7,588,592 B2 * | 9/2009 | Winslow et al. | 606/249 |
| 7,666,228 B2 | 2/2010 | Le Couedic et al. | |
| 7,727,233 B2 * | 6/2010 | Blackwell et al. | 606/71 |
| 7,857,857 B2 | 12/2010 | Kim | |
| 7,862,592 B2 | 1/2011 | Peterson et al. | |
| 7,871,426 B2 * | 1/2011 | Chin et al. | 606/248 |
| 7,935,133 B2 * | 5/2011 | Malek | 606/249 |
| 7,955,392 B2 * | 6/2011 | Dewey et al. | 623/17.16 |
| 8,043,337 B2 * | 10/2011 | Klyce et al. | 606/252 |
| 8,048,120 B1 | 11/2011 | Fallin et al. | |
| 8,070,817 B2 | 12/2011 | Gradl et al. | |
| 8,114,132 B2 * | 2/2012 | Lyons et al. | 606/249 |
| 8,128,659 B2 * | 3/2012 | Ginsberg et al. | 606/246 |
| 8,157,842 B2 * | 4/2012 | Phan et al. | 606/249 |
| 8,206,420 B2 * | 6/2012 | Patel et al. | 606/249 |
| 8,636,772 B2 * | 1/2014 | Schmierer et al. | 606/248 |
| 2001/0020188 A1 | 9/2001 | Sander | |
| 2003/0040746 A1 * | 2/2003 | Mitchell et al. | 606/61 |
| 2003/0045877 A1 * | 3/2003 | Yeh | 606/61 |
| 2003/0216736 A1 * | 11/2003 | Robinson et al. | 606/61 |
| 2004/0034430 A1 | 2/2004 | Falahee | |
| 2004/0106995 A1 | 6/2004 | Le Couedic et al. | |
| 2004/0193272 A1 | 9/2004 | Zubok et al. | |
| 2005/0043732 A1 | 2/2005 | Dalton | |
| 2005/0137594 A1 | 6/2005 | Doubler et al. | |
| 2005/0187632 A1 | 8/2005 | Zubok et al. | |
| 2005/0216017 A1 | 9/2005 | Fielding et al. | |
| 2005/0234459 A1 * | 10/2005 | Falahee et al. | 606/72 |
| 2005/0256582 A1 | 11/2005 | Ferree | |
| 2006/0004367 A1 | 1/2006 | Alamin et al. | |
| 2006/0074425 A1 | 4/2006 | Sutterlin et al. | |
| 2006/0142771 A1 | 6/2006 | Beutter | |
| 2006/0235391 A1 | 10/2006 | Sutterlin | |
| 2006/0235518 A1 | 10/2006 | Blain | |
| 2006/0241601 A1 * | 10/2006 | Trautwein et al. | 606/61 |
| 2006/0247623 A1 | 11/2006 | Anderson et al. | |
| 2006/0247634 A1 | 11/2006 | Warner et al. | |
| 2006/0247640 A1 * | 11/2006 | Blackwell et al. | 606/71 |
| 2006/0287654 A1 | 12/2006 | Posnick | |
| 2007/0016189 A1 | 1/2007 | Lake et al. | |
| 2007/0093823 A1 | 4/2007 | Booth et al. | |
| 2007/0162001 A1 | 7/2007 | Chin et al. | |
| 2007/0173936 A1 | 7/2007 | Hester et al. | |
| 2007/0179500 A1 | 8/2007 | Chin et al. | |
| 2007/0191844 A1 | 8/2007 | Carls et al. | |
| 2007/0233082 A1 | 10/2007 | Chin et al. | |
| 2007/0250065 A1 | 10/2007 | Efron et al. | |
| 2007/0270812 A1 | 11/2007 | Peckham | |
| 2007/0270840 A1 * | 11/2007 | Chin et al. | 606/61 |
| 2007/0276384 A1 | 11/2007 | Spratt | |
| 2007/0276500 A1 | 11/2007 | Zucherman et al. | |
| 2008/0021471 A1 | 1/2008 | Winslow | |
| 2008/0021472 A1 * | 1/2008 | Winslow et al. | 606/61 |
| 2008/0103512 A1 | 5/2008 | Gately | |
| 2008/0140125 A1 * | 6/2008 | Mitchell et al. | 606/279 |
| 2008/0147190 A1 * | 6/2008 | Dewey et al. | 623/17.16 |
| 2008/0177330 A1 * | 7/2008 | Ralph et al. | 606/290 |
| 2008/0183211 A1 * | 7/2008 | Lamborne et al. | 606/249 |
| 2008/0183218 A1 * | 7/2008 | Mueller et al. | 606/280 |
| 2008/0228225 A1 | 9/2008 | Trautwein et al. | |
| 2008/0243185 A1 * | 10/2008 | Felix et al. | 606/246 |
| 2008/0243186 A1 * | 10/2008 | Abdou | 606/246 |
| 2008/0269804 A1 * | 10/2008 | Holt | 606/254 |
| 2008/0281359 A1 * | 11/2008 | Abdou | 606/246 |
| 2009/0018658 A1 | 1/2009 | Garcia | |
| 2009/0062918 A1 | 3/2009 | Wang et al. | |
| 2009/0216272 A1 | 8/2009 | Currier et al. | |
| 2009/0216273 A1 | 8/2009 | Cox | |
| 2009/0264927 A1 * | 10/2009 | Ginsberg et al. | 606/246 |
| 2009/0270918 A1 | 10/2009 | Attia et al. | |
| 2009/0326589 A1 | 12/2009 | Lemoine et al. | 606/280 |
| 2010/0036419 A1 * | 2/2010 | Patel et al. | 606/249 |
| 2010/0087860 A1 * | 4/2010 | Chin et al. | 606/249 |
| 2010/0241167 A1 * | 9/2010 | Taber et al. | 606/249 |
| 2010/0318127 A1 * | 12/2010 | Phan et al. | 606/249 |
| 2011/0029020 A1 * | 2/2011 | Gordon et al. | 606/248 |
| 2011/0054531 A1 * | 3/2011 | Lamborne et al. | 606/249 |
| 2011/0066186 A1 * | 3/2011 | Boyer et al. | 606/249 |
| 2011/0144692 A1 * | 6/2011 | Saladin et al. | 606/249 |
| 2011/0166600 A1 * | 7/2011 | Lamborne et al. | 606/249 |
| 2011/0224731 A1 * | 9/2011 | Smisson et al. | 606/249 |
| 2011/0224740 A1 | 9/2011 | Smisson, III et al. | |
| 2011/0313458 A1 * | 12/2011 | Butler et al. | 606/249 |
| 2011/0319936 A1 * | 12/2011 | Gordon et al. | 606/248 |

(56) References Cited

U.S. PATENT DOCUMENTS

| | | | |
|---|---|---|---|
| 2012/0010662 A1* | 1/2012 | O'Neil et al. | 606/279 |
| 2012/0016418 A1* | 1/2012 | Chin et al. | 606/249 |
| 2012/0078304 A1* | 3/2012 | Jensen et al. | 606/251 |
| 2012/0078305 A1* | 3/2012 | Wang et al. | 606/257 |
| 2012/0083844 A1* | 4/2012 | Linares | 606/249 |
| 2012/0083846 A1* | 4/2012 | Wallenstein et al. | 606/279 |
| 2012/0089184 A1* | 4/2012 | Yeh | 606/248 |
| 2012/0095512 A1* | 4/2012 | Nihalani | 606/251 |
| 2012/0101528 A1* | 4/2012 | Souza et al. | 606/249 |
| 2012/0109198 A1* | 5/2012 | Dryer et al. | 606/248 |
| 2012/0109203 A1* | 5/2012 | Dryer et al. | 606/249 |
| 2012/0109205 A1* | 5/2012 | Mitchell et al. | 606/249 |
| 2012/0123475 A1* | 5/2012 | Ahn et al. | 606/246 |
| 2012/0136390 A1* | 5/2012 | Butler et al. | 606/248 |
| 2012/0143252 A1* | 6/2012 | Robinson | 606/248 |
| 2012/0150228 A1* | 6/2012 | Zappacosta et al. | 606/248 |
| 2012/0158061 A1* | 6/2012 | Koch et al. | 606/248 |
| 2012/0158063 A1* | 6/2012 | Altarac et al. | 606/249 |
| 2012/0310292 A1 | 12/2012 | Smisson, III et al. | |

FOREIGN PATENT DOCUMENTS

| | | | |
|---|---|---|---|
| WO | WO-00/62693 A1 | 10/2000 | |
| WO | WO 03/007829 A1 | 1/2003 | |
| WO | WO03007829 | 1/2003 | |
| WO | WO 2007/070819 A1 | 6/2007 | |
| WO | WO2007109402 | 9/2007 | |
| WO | WO-/2008/022471 A1 | 2/2008 | |
| WO | WO-2009/086397 A2 | 7/2009 | |
| WO | WO-2010056355 A2 | 5/2010 | |

OTHER PUBLICATIONS

Examination Report issued for Australian Patent Application No. 2010282649, dated Nov. 27, 2014, 4 pages.

Office Action issued for Japanese Patent Application No. 2012-524787, dated May 13, 2014, 4 pages (with English language translation).

"Globus Medical; SP-Fix Spinous Process Fixation Plate: Surgical Technique, pp. 1-32 Jan. 2011".

"OHSU Surgeons Find New Way to Fix Painful Broken Ribs," Oregon Health & Science University, http://www.ohsu.edu.ohsuedu/newspub/releases/062706ribs.cfm, Jun. 27, 2006.

Bostman et al., "Posterior Spinal Fusion Using Internal Fixation with the Daab Plate," Acta. Orthop. Scand., vol. 55, pp. 310-314, 1984.

International Search Report and Written Opinion issued in International Application No. PCT/US08/88204, mailed Feb. 12, 2009.

International Search Report and Written Opinion issued in international Application No. PCT/US2008/088196, mailed Apr. 23, 2009.

Lanx, "Aspen Spinous Process System Product Brochure," www.lanx.com, Dec. 16, 2008.

Lanx, "Aspen Spinous Process System," http://www.spineansi.com/080607_Aspen_Lab_Presentation.ppt, last accessed Jun. 10, 1999.

Saint John's Health Center, "Saint John's Spine Surgeion Uses ILIF Procedure to Treat Lumbar Spinal Stenosis," www.medicalnewstoday.com/articles/155013.php.

Sénégas, "Minimally Invasive Dynamic Stabilisation of the Lumbar Motion Segment with an Interspinous Implant," Minimally Invasive Spine Surgery, pp. 459-465, 2006.

U.S. Appl. No. 60/724,632 entitled "Inter-spinous Orthopedic Device Placement and Method of Use," filed Oct. 7, 2005.

Australian Patent Examination Report No. 2, issued on Apr. 24, 2015, 7 pages.

\* cited by examiner

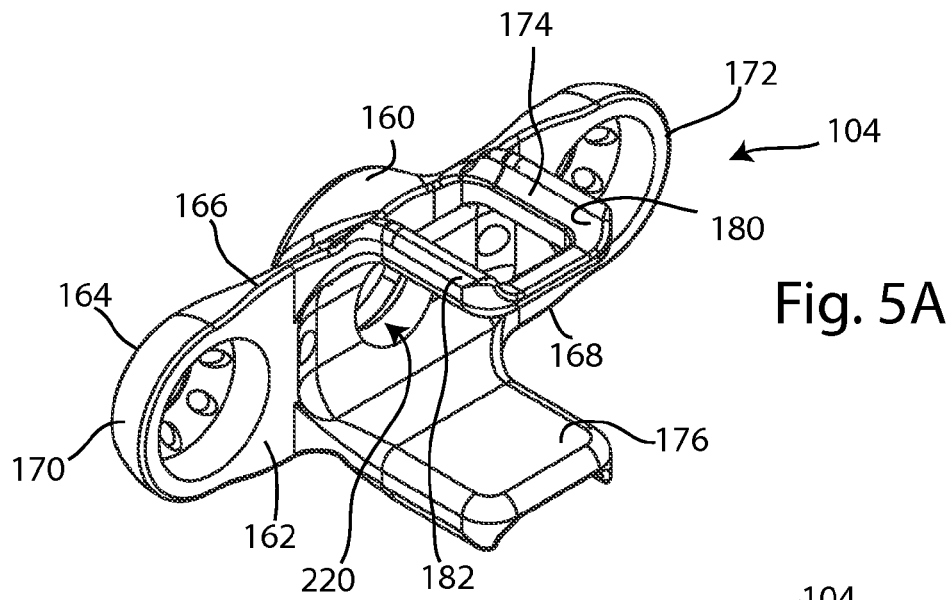
Fig. 5A
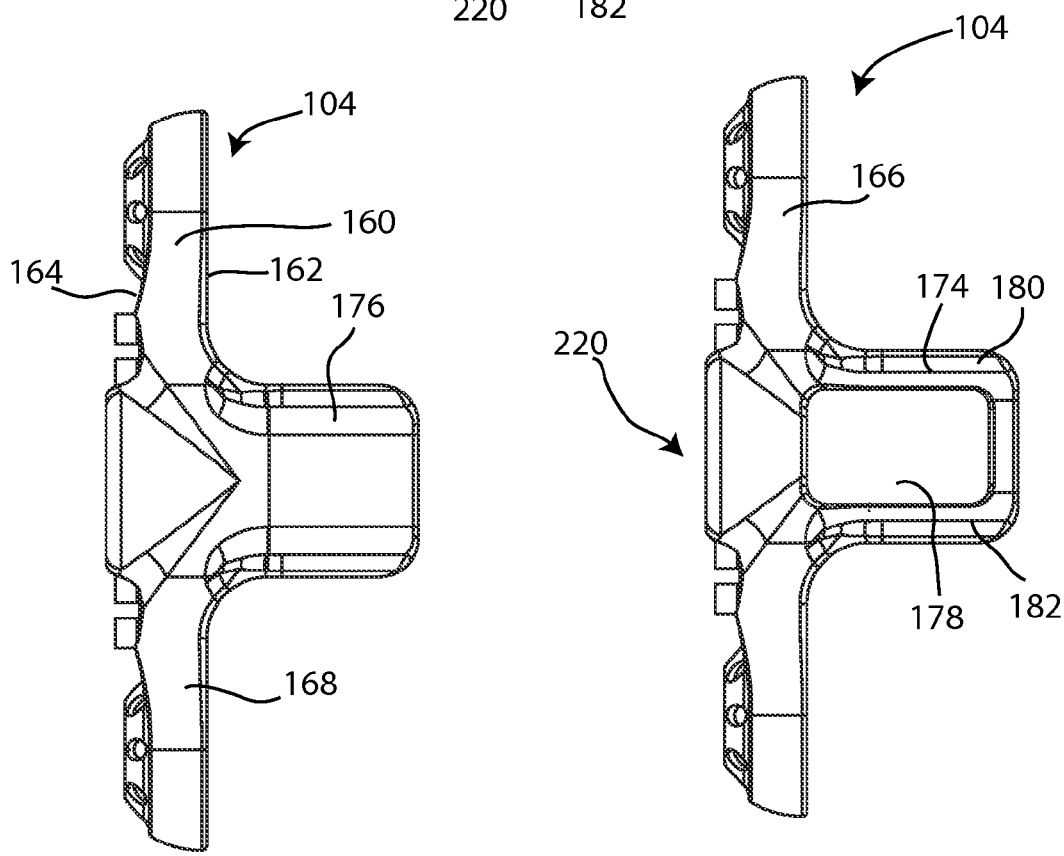
Fig. 5B
Fig. 5C

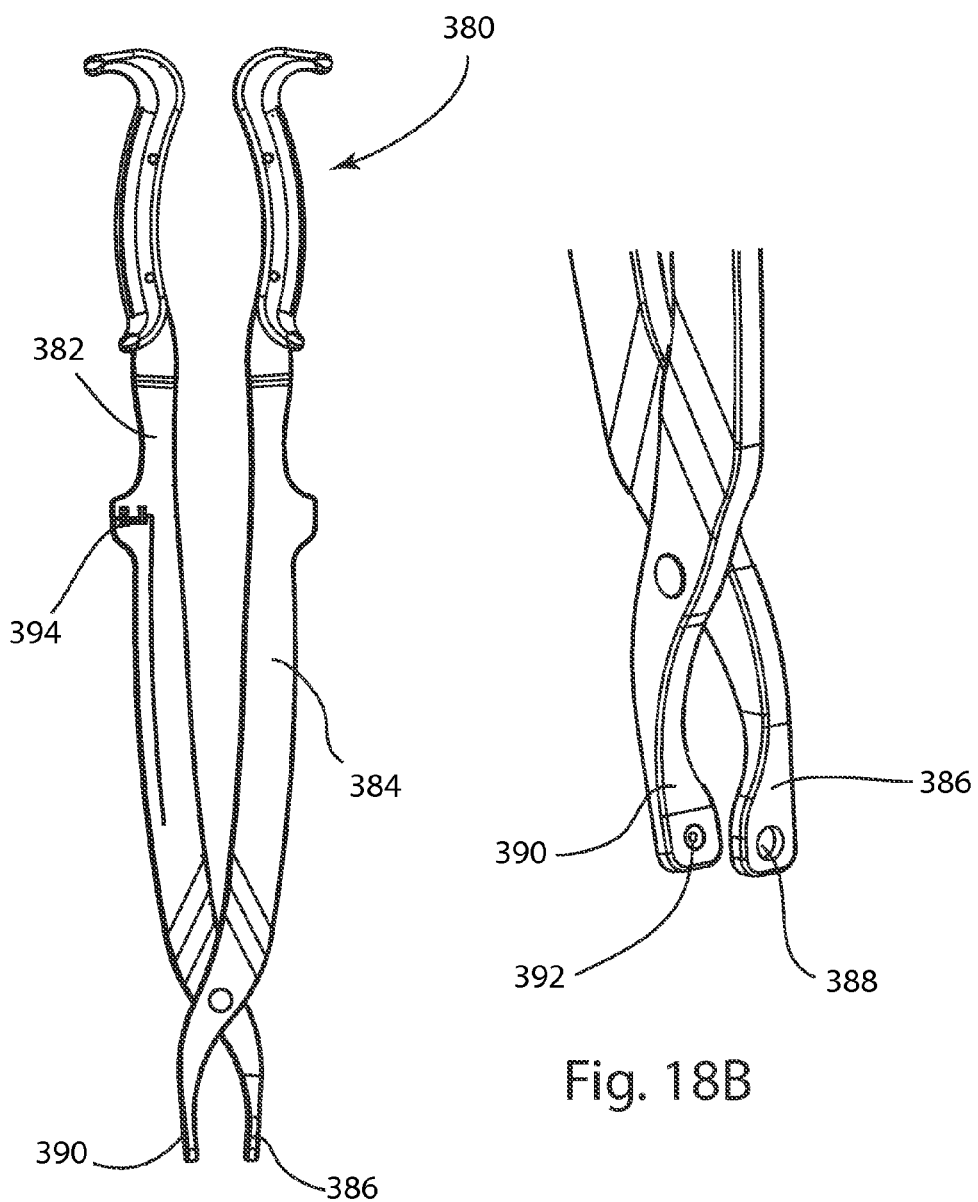

SPINOUS PROCESS FUSION IMPLANTS

CROSS-REFERENCE TO RELATED APPLICATIONS

This application is a continuation-in-part of:
pending prior U.S. patent application Ser. No. 12/820,575 filed Jun. 22, 2010 and entitled BONE TISSUE CLAMP, which claims the benefit of:
prior Provisional U.S. Patent Application Ser. No. 61/219,687, filed Jun. 23, 2009 and entitled BONE TISSUE CLAMP.
This application also claims the benefit of Provisional U.S. Patent Application No. 61/232,692, filed Aug. 10, 2009, entitled SPINOUS PROCESS FUSION IMPLANTS; and
Provisional U.S. Patent Application No. 61/366,755, filed Jul. 22, 2010, entitled INSERTION, COMPRESSION AND LOCKING INSTRUMENTATION.
The above-referenced documents are hereby incorporated by reference in their entirety.

FIELD OF THE INVENTION

The present invention relates generally to bone plates, and more specifically to bone fusion procedures in which two or more bone portions are stabilized in order to promote the development of a bony fusion mass.

BACKGROUND OF THE INVENTION

A normal, healthy bone typically has complex surface geometry which is dictated by the function of the bone in the body. The surface of a bone rarely forms a regular geometric shape, such as a plane, cylinder, cone, or sphere. This phenomenon is exacerbated in diseased, damaged, or deformed bones. Even when a portion of a bone is removed, or resected, the cut surface may be irregular. When a bone is fractured, the potential for irregular fragments is high. Similar surfaces on adjacent bones may be a different shape and size, and are often not precisely aligned. For all these reasons, it can be challenging to fit a bone plate to bone surfaces securely enough to stabilize a developing fusion mass. This is especially true if the bone plate is designed as a regular geometric shape, such as a rectangular solid. The present invention provides an apparatus that automatically adjusts itself to fit congruently on irregular bone surfaces.

Bone plates are often secured to bone with screws, pegs, or other fixation elements. A common characteristic of these fixation elements is that they invasively penetrate the surface of the bone in order to achieve fixation. When removed, or revised, they leave behind defects which may limit the surgical options for subsequent procedures. These types of fixation elements usually rely at least in part on cancellous bone for their fixation strength. However, cancellous bone is notoriously variable in quality. Cortical bone is a superior load bearing material compared to cancellous bone. However, in many locations on the skeleton, cortical bone is distributed in a relatively thin layer. Furthermore, precisely because cortical bone is a strong load bearing material, it can be difficult to seat a cortical fixation element unless the fixation element is aligned with the cortical surface. The present invention provides an apparatus that achieves fixation in cortical bone without collateral damage to cortical or cancellous bone.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope.

Identical reference numerals do not necessarily indicate an identical structure. Rather, the same reference numeral may be used to indicate a similar feature or a feature with similar functionality. Not every feature of each embodiment is labeled in every figure in which that embodiment appears, in order to keep the figures clear.

FIG. 5A is an isometric view of the second plate of the spinous process fusion implant of FIG. 1; FIG. 5B is a side view of the second plate of FIG. 5A; FIG. 5C is an opposite side view of the second plate of FIG. 5B;

FIG. 18A is a side view of a second instrument for providing locking force; FIG. 18B is an isometric view of a working end of the instrument of FIG. 18A.

DETAILED DESCRIPTION

Figure 1:
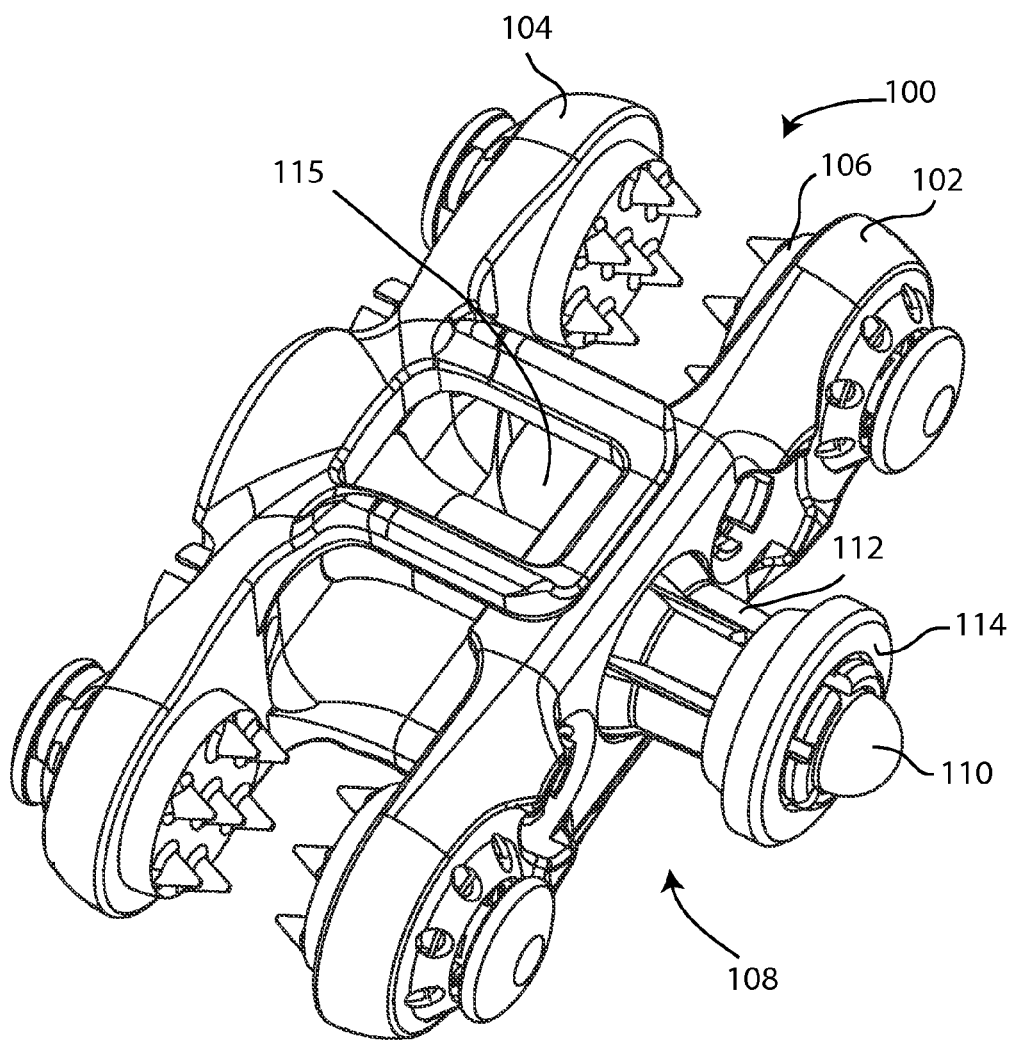
FIG. 1 is an isometric view of a spinous process fusion implant including a first plate, a second plate, a plurality of fixation pads and a locking mechanism, the implant in an unlocked configuration.

While exemplary embodiments of the present invention have been shown and described in detail below, it will be clear to the person skilled in the art that changes and modifications may be made without departing from the scope of the invention. As such, that which is set forth in the following description and accompanying drawings is offered by way of illustration only and not as a limitation. The actual scope of the invention is intended to be defined by the following claims, along with the full range of equivalents to which such claims are entitled.

In addition, one of ordinary skill in the art will appreciate upon reading and understanding this disclosure that other variations for the invention described herein can be included within the scope of the present invention.

In the following Detailed Description, various features are grouped together in several embodiments for the purpose of streamlining the disclosure. This method of disclosure is not to be interpreted as reflecting an intention that exemplary embodiments of the invention require more features than are expressly recited in each claim. Rather, as the following claims reflect, inventive subject matter may lie in less than all features of a single disclosed embodiment. Thus, the following claims are hereby incorporated into the Detailed Description, with each claim standing on its own as a separate embodiment.

Standard medical planes of reference and descriptive terminology are employed in this specification. While these terms are commonly used to refer to the human body, certain terms are broadly applicable to physical objects in general. A sagittal plane divides a body into right and left portions. A mid-sagittal plane divides a body into equal right and left halves. A coronal plane divides a body into anterior and posterior portions. A transverse plane divides a body into superior and inferior portions. Anterior means toward the front of a body. Posterior means toward the back of a body. Superior or cephalad means toward the head. Inferior or caudal means toward the feet. Medial means toward the midline of a body. Lateral means away from the midline of a body. Axial means toward a central axis of a body. Abaxial means away from a central axis of a body. Generally parallel means an angle of 0 degrees, plus or minus 45 degrees. Generally perpendicular means an angle of 90 degrees, plus or minus 45 degrees. Oblique means an angle between 0 degrees and 90 degrees, i.e., neither perpendicular nor parallel.

In this application, polyaxial rotation is rotation that can occur about at least two axes that are not parallel to each other. Triaxial rotation is rotation about three perpendicular axes. Triaxial rotation is equivalent to rotation about a point, because free rotation about any axis of a 3D coordinate system is the same as rotation that is not limited to any axis in the system. A polyaxial connection permits a component to be rotated with respect to another component around more than one axis. Polyaxial may be synonymous with multiaxial, a multiaxial joint being a joint in which movement occurs in a number of axes. Examples of polyaxial connections include a ball-and-socket joint such as a hip, and ellipsoid joint such as the humerus/glenoid or the wrist, a universal joint, a two axis gimbal set, and a Canfield joint among other polyaxial connections known in the art. A swivel is a connection that allows the connected object, such as a gun or chair, to rotate horizontally and/or vertically.

A pad is a component of a clamping device designed to directly contact a surface of a workpiece to transfer pressure from the clamp to the workpiece. A swivel pad is a component of a clamping device designed to rotate to congruently contact a surface of a workpiece when pressure is applied with the clamp.

A great circle of a sphere is a circle that runs along the surface of that sphere so as to cut it into two equal halves. Great circle, major diameter, and equator may all be synonymous.

An obverse side is the more conspicuous or significant of two sides of an object. For example, in numismatics, the obverse of a coin is the front, main, top, or "heads" side, usually bearing a portrait. A reverse side is the corresponding less conspicuous or significant side. For example, the reverse of a coin is the back, bottom, or "tails" side. In this application, a side may be considered significant because it faces toward a surgical attachment site, such as a bony structure.

Undercut means to cut away material from the underside of an object or feature so as to leave an overhanging portion in relief.

Elastic deformation means a deformation of a body in which the applied stress is small enough so that the object retains its original dimensions once the stress is released.

The term "coupled" is defined as connected, although not necessarily directly, and not necessarily mechanically.

The use of the word "a" or "an" when used in conjunction with the term "comprising" in the claims and/or the specification may mean "one," but it is also consistent with the meaning of "one or more" or "at least one." The term "about" means, in general, the stated value plus or minus 5%. The use of the term "or" in the claims is used to mean "and/or" unless explicitly indicated to refer to alternatives only or the alternative are mutually exclusive, although the disclosure supports a definition that refers to only alternatives and "and/or."

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a method or device that "comprises," "has," "includes" or "contains" one or more steps or elements, possesses those one or more steps or elements, but is not limited to possessing only those one or more elements. Likewise, a step of a method or an element of a device that "comprises," "has," "includes" or "contains" one or more features, possesses those one or more features, but is not limited to possessing only those one or more features. Furthermore, a device or structure that is configured in a certain way is configured in at least that way, but may also be configured in ways that are not listed.

According to a first aspect, the present invention provides a bone plate assembly including a plate, the plate including an obverse side, a reverse side, and a pivot element, the reverse side opposite the obverse side, and a pad carried by the plate.

The pad includes a bearing face and a pivot feature, the bearing face adjacent the obverse side, the pivot feature engaging the pivot element so that the pad rotates relative to the plate.

In an embodiment, the bone plate assembly includes a spacer, in an initial configuration, the spacer prevents unintentional locking of the pad to the plate; wherein, in a final configuration, the spacer permits intentional locking of the pad to the plate.

In an embodiment, the bone plate assembly includes a retainer, the retainer keeping the pad coupled to the plate.

In an embodiment, the pad rotates relative to the plate through a range of motion, the range of motion comprising a neutral position and a tilted position, the bearing face parallel to the obverse side in the neutral position, the bearing face oblique to the obverse side in the tilted position.

In an embodiment, the pad rotates polyaxially relative to the plate.

In an embodiment, the pivot element includes a conical socket and the pivot feature includes a spherical protrusion. The spherical protrusion rotates polyaxially in the conical socket.

In an embodiment, the bone plate assembly includes an initial configuration, in which the pad freely rotates relative to the plate, and a final configuration, in which the pad is locked to the plate.

In an embodiment, the spacer includes a flange on the pad.

In an embodiment, in the initial configuration, the spacer holds the pivot feature spaced apart from the pivot element, and in the final configuration, the spacer deforms as the pivot feature is urged against the pivot element.

In an embodiment, the pad is urged into position for locking with the plate when a spacer deflecting force is applied to the pad, the pad locking with the plate when a pad locking force is applied to the pad, the pad locking force being greater than the spacer deflecting force.

In an embodiment, the pad is captive to the plate.

In an embodiment, the plate includes an aperture, the retainer including a cap on the pad, the cap spaced apart from the bearing face, the pad extending through the aperture so that the aperture is between the bearing face and the cap, the aperture being smaller than the bearing face and the cap.

In an embodiment, the bone plate assembly includes a plurality of pads.

According to a second aspect, the present invention provides a plate assembly for attachment to a bone surface, including a first plate including a first obverse side and a first reverse side opposite the first obverse side, a second plate including a second obverse side and a second reverse side opposite the second obverse side, and a locking mechanism coupling the first plate to the second plate so that the second obverse side faces the first obverse side. The plate assembly has an unlocked configuration and a first locked configuration. In the unlocked configuration, the first plate rotates and translates relative to the second plate to align the first plate to the bone surface. In the first locked configuration, the first plate is rotationally and translationally fixed relative to the second plate.

In an embodiment, the plate assembly includes a post secured to the second plate in a fixed rotational alignment, the post extending generally perpendicular to the obverse side of the second plate. The first plate includes a conical socket, the post extending through the socket. The locking mechanism includes a collet, the collet including a spherical protrusion, the post extending through the collet. In the first locked configuration, the spherical protrusion wedges between the conical socket and the post.

In an embodiment, in the unlocked configuration, the first plate polyaxially rotates relative to the second plate.

In an embodiment, in the unlocked configuration, the first plate polyaxially rotates relative to the locking mechanism.

In an embodiment, the first plate includes a conical socket, and the locking mechanism includes a spherical protrusion. In the unlocked configuration, the conical socket rotates polyaxially on the spherical protrusion.

In an embodiment, the locking mechanism includes a collet. In the unlocked configuration, the first plate and the collet translate relative to the second plate.

In an embodiment, the plate assembly includes a post coupled to the second plate in a fixed rotational alignment, the post extending generally perpendicular to the obverse side of the second plate. In the unlocked configuration, the first plate and the collet translate along the post.

In an embodiment, the first plate is rotationally and translationally fixed to the locking mechanism.

In an embodiment, the post includes a protrusion, the protrusion frictionally engaging the second plate to retain the post on the second plate.

In an embodiment, the locking mechanism includes a ring, and the collet includes a frustoconical shaft adjoining the spherical protrusion. The frustoconical shaft extends through the ring. The plate assembly has a second locked configuration. In the second locked configuration, the frustoconical shaft is wedged between the ring and the post.

In an embodiment, the plate assembly includes a first wall extending between the first and second plates, the first wall generally perpendicular to a selected one of the first and second obverse sides, the first wall contiguous with a first edge of the selected obverse side, the first wall terminating in a first free end adjacent to the other one of the first and second plates.

In an embodiment, the plate assembly includes a second wall similar to the first wall, the second wall extending between the first and second plates, the second wall generally perpendicular to the selected obverse side, the second wall contiguous with a second edge of the selected obverse side opposite the first edge, the second wall terminating in a second free end adjacent to the to the other one of the first and second plates.

In an embodiment, the first wall includes a pair of opposing edges, each one of the pair of edges protruding from a lateral aspect of the first wall so as to form an open channel extending from the edge of the selected obverse side to the free end.

In an embodiment, the first wall includes a window.

According to a third aspect, the present invention provides a pad including a polyaxial feature, a bearing face, and a spacer feature.

In an embodiment, the pad has a retainer feature.

In an embodiment, the polyaxial feature has a spherical surface.

In an embodiment, the pad has a protrusion projecting from the bearing face, the protrusion selected from the group consisting of spikes, barbs, pins, prongs, pegs, teeth, ridges, tines, and knurling.

In an embodiment, the retainer feature prevents unintentional disassembly of the pad from the supporting structure when the pad is assembled with a supporting structure.

In an embodiment, the spacer feature has an original configuration and a deflected configuration. In the deflected configuration, at least a portion of the spacer feature is closer to the polyaxial feature than in the original configuration.

In an embodiment, the spacer feature deflects to position the polyaxial feature for locking with a corresponding polyaxial element of a supporting structure when a spacer deflecting force is applied to the pad, the polyaxial feature locks with the corresponding polyaxial element of the supporting structure when a pad locking force is applied to the pad, and the pad locking force is greater than the spacer deflecting force.

In an embodiment, the spacer feature prevents unintentional locking of the polyaxial feature with a corresponding polyaxial element of the supporting structure when the pad is assembled with a supporting structure.

In an embodiment, the spacer feature touches the supporting structure and the polyaxial feature is spaced apart from the corresponding polyaxial element of the supporting structure when the pad is assembled with the supporting structure.

In an embodiment, the polyaxial feature locks with a corresponding polyaxial element of a supporting structure when the polyaxial feature is urged toward the polyaxial element.

According to a fourth aspect, the present invention provides a bone plate including an obverse side, a reverse side opposite the obverse side, a first polyaxial element, and a retainer element.

In an embodiment, the bone plate includes a second polyaxial element.

In an embodiment, the bone plate includes a wall extending from an edge of the obverse side, the wall generally perpendicular to the obverse side, the wall terminating in a free end opposite the edge of the obverse side.

In an embodiment, the bone plate includes a pin extending from the obverse side, the pin generally perpendicular to the obverse side.

In an embodiment, the bone plate includes an instrument connector. The instrument connector couples to a corresponding plate connector of an instrument to hold the plate on the instrument.

In an embodiment, the first polyaxial element opens toward the obverse side.

In an embodiment, the first polyaxial element includes a first frustoconical surface.

In an embodiment, when the plate is assembled with a pad, the retainer element prevents unintentional disassembly of the plate from the pad.

In an embodiment, the retainer element includes a flange.

In an embodiment, the bone plate includes an aperture through the flange.

In an embodiment, the second polyaxial element opens toward the reverse side.

In an embodiment, the second polyaxial element includes a second frustoconical surface.

In an embodiment, the bone plate includes a retainer adjacent to the second polyaxial element. The retainer prevents unintentional disassembly of a corresponding polyaxial component from the plate.

In an embodiment, the retainer adjacent to the second polyaxial element includes a rim adjacent to the reverse side, the rim forming a constriction adjacent to the second polyaxial element.

In an embodiment, the wall includes a pair of opposing edges, each one of the pair of edges protruding from a lateral aspect of the wall so as to form an open channel extending from the edge of the obverse side to the free end.

In an embodiment, the wall includes a window.

In an embodiment, the bone plate includes a pin connector, the pin connector holding the pin to the plate in a fixed rotational alignment.

In an embodiment, the pin connector includes an aperture through the plate from the obverse side to the reverse side, and a counterbore on the reverse side around the aperture.

In an embodiment, the instrument connector includes a socket.

In an embodiment, a first end of the socket is formed into a plurality of tabs. The tabs grip the plate connector.

In an embodiment, the socket includes a second end opposite the first end, and a middle portion between the first and second ends, the middle portion undercutting the first end.

In an embodiment, the middle portion is wider than the second end.

Referring to FIG. 1, an isometric view shows a spinal fusion implant according to one embodiment of the invention, in an unlocked configuration. Spinal implant 100 includes two plates 102, 104, a plurality of pads 106, and a locking mechanism 108. Plate 102 may be a first plate or a flat plate, and plate 104 may be a second plate, or an extension plate. Locking mechanism 108 may rigidly lock the positions of plates 102, 104 relative to one another. Locking mechanism 108 includes post 110, collet 112, and ring 114. At least one of the two plates may polyaxially rotate relative to the other before the locking mechanism is actuated to lock the plates in a fixed relationship. Additionally, each pad is lockable to a plate, and may polyaxially rotate relative to the plate before being locked to the plate in a fixed relationship. A pad may be also termed a fixation pad, foot, or grip. The spinal fusion implant may be termed a bone plate assembly. A bone plate assembly may also include a bone plate in combination with any of the fixation or locking features disclosed herein.

Figure 2:
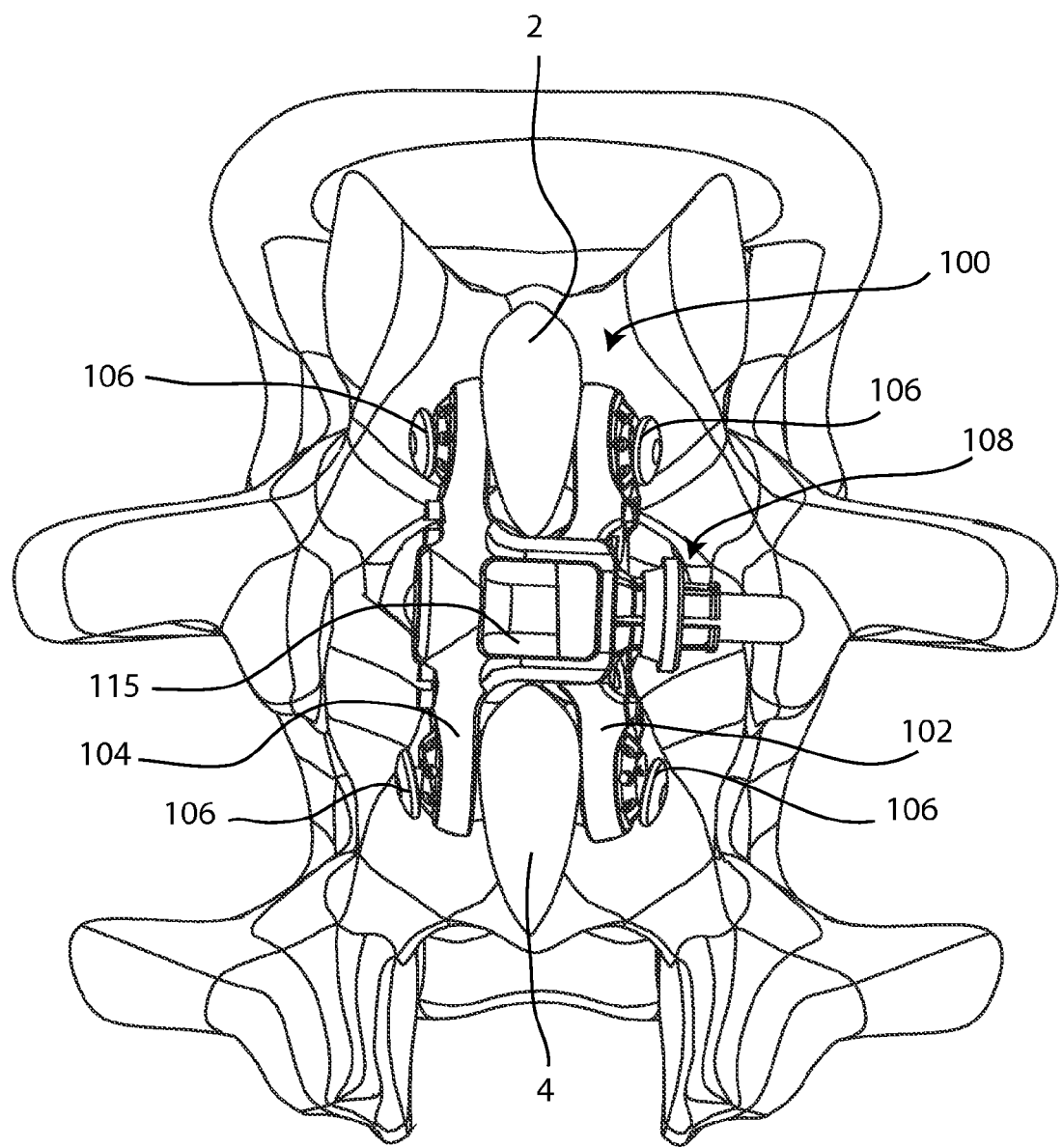
FIG. 2 is a posterior view of the spinous process fusion implant of FIG. 1 implanted between two spinous processes, the implant in a locked configuration, the first plate and the fixation pads polyaxially adjusted to match the spinal anatomy.

As shown in FIG. 2, spinal implant 100 may be implanted in a portion of a spine to promote fusion between two spinous processes 2, 4. Each plate 102, 104 may be positioned to extend cephalad-caudally from a superior, or first spinous process to an inferior, or second spinous process, along a lateral side of the two spinous processes. Each pad 106 may be positioned to extend through an aperture in one of the plates and bear against a lateral side of one of the spinous process. Selective forces may be applied to compress the pads toward the spinous processes, and lock the pads to the plates. The locking mechanism 108 extends transversely between the two spinous processes and couples the plates together, and when a selected force is applied, locks the plates together. An opening in at least one plate provides a window for introduction of bone graft material into a chamber 115 formed between the plates and the spinous processes to further promote fusion between the spinous processes. Although one implant is shown coupled to two spinous processes, it is appreciated that other embodiments may be coupled to multiple processes, providing fusion across multiple spinal segments. In an alternative embodiment, one or more of the plates may be sized and shaped to extend along at least three spinous processes, and accommodate at least three pads and two locking mechanisms. In another embodiment, multiple spinal implants 100 may be coupled to a series of spinous processes; at least one of the implants 100 may be angled to allow room for more than one implant to be coupled to a single spinous process. It is also appreciated that spinal implant 100 or an alternate embodiment may be coupled to adjacent transverse processes, inferior or superior facets, vertebral bodies, or two other bony structures such as ribs, within the scope of the invention.

Figure 3:
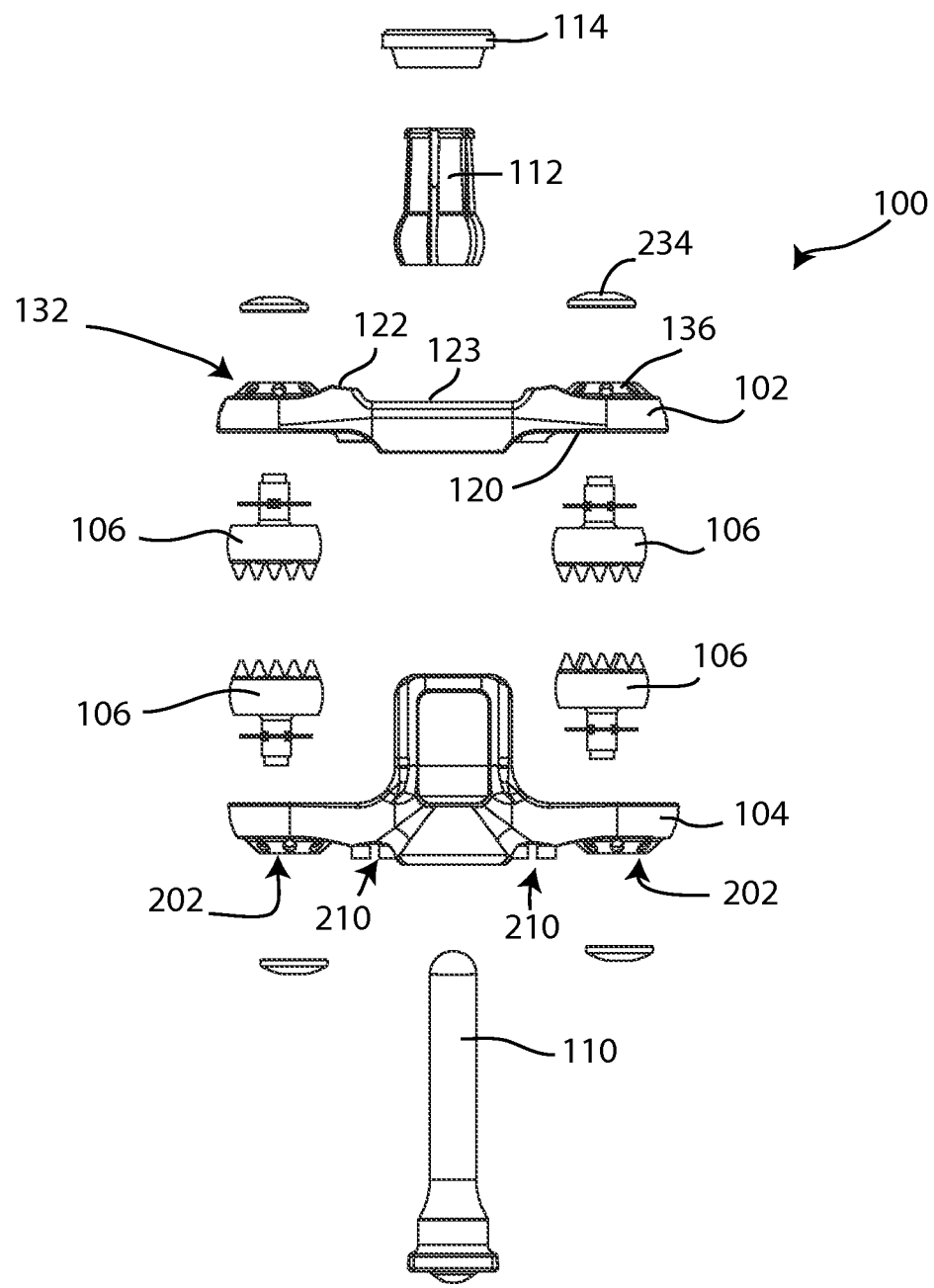
FIG. 3 is an exploded view of the spinous process fusion implant of FIG. 1.

FIG. 3 provides an exploded view of spinal implant 100 to show the relative arrangement of the component parts. Although four fixation pads 106 are depicted in the embodiment shown, it is appreciated that in other embodiments fewer or more fixation pads may be included. Additionally, other embodiments may include other types of fixation, including but not limited to bone screws, pedicle screws, hooks, and clamps. Types of fixation may be mixed within a single embodiment.

Figure 4A:
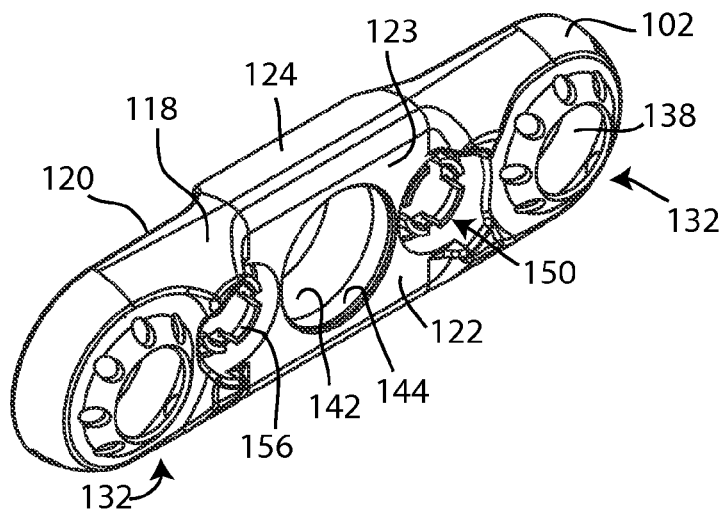
FIG. 4A is an isometric view of the first plate of the spinous process fusion implant of FIG. 1.
Figure 4B:
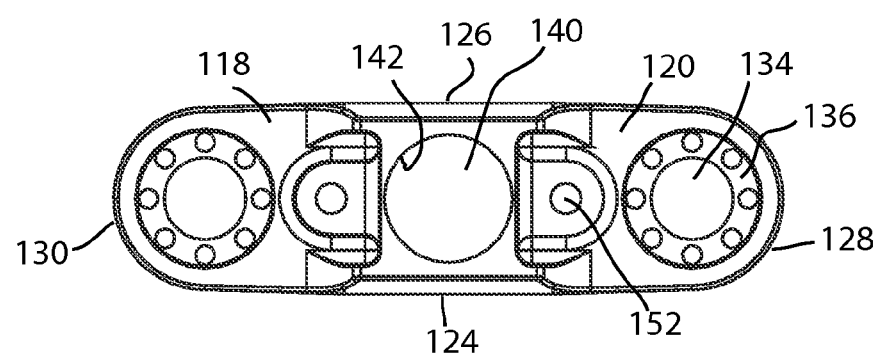
FIG. 4B is a view of an obverse side of the plate of FIG. 4A.
Figure 4C:
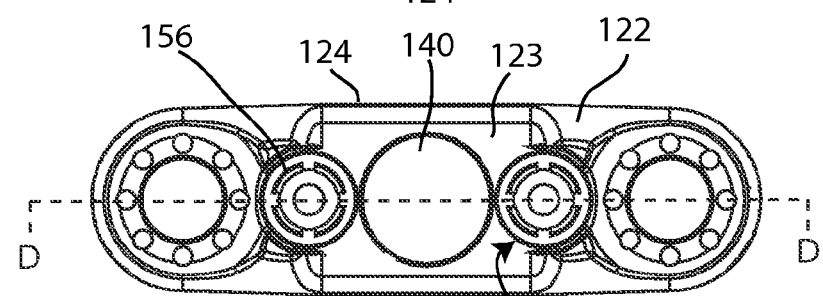
FIG. 4C is a view of a reverse side of the plate of FIG. 4A.
Figure 4D:
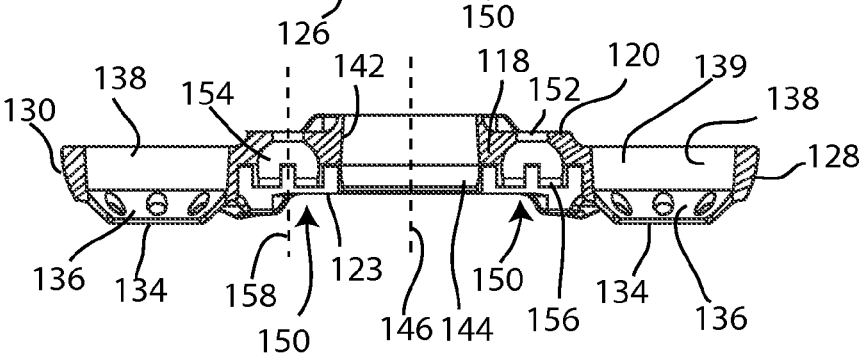
FIG. 4D is a cross-sectional view of the plate of FIG. 4C taken along section line D-D.

FIG. 4A is an isometric view of plate 102, while FIG. 4B is an obverse side view of plate 102; FIG. 4C is a reverse side view of the plate 102; and FIG. 4D is a cross-sectional view taken along section line D-D shown in FIG. 4C. Plate 102, which may be a supporting structure, includes a generally elongated plate body 118 having a first, or obverse side 120, and a second, or reverse side 122, opposite the obverse side. When implanted according to one embodiment of the invention as shown in FIG. 2, the obverse side 120 is a bone-facing side. A portion of the reverse side 122 is occupied by a recess 123. The recess 123 may advantageously afford more room for the collet 112 and ring 114 when the implant 100 is implanted in a portion of a spine, than if the reverse side were not recessed. Plate 102 is bounded by a first plate edge 124, a second plate edge 126, a first plate end 128 and a second plate end 130. It is appreciated that in the embodiment shown, plate 102 is bilaterally symmetrical; however in other embodiments the positioning of features of the plate may vary to provide a symmetrical or a non-symmetrical plate.

Plate 102 includes at least one polyaxial element which may provide for pivoting or polyaxial connection of a pad 106 to the plate, wherein the pad may be positioned at any of a continuum of positions relative to the plate upon locking attachment to the plate. Each polyaxial element 132, which may also be termed a pivot element, includes an aperture 134 extending through an annular flange 136. In the embodiment shown, flange 136 is domed such that it protrudes convexly on the reverse side 122 of the plate, and is recessed concavely on the obverse side 120 of the plate. Adjacent the flange 136 on the obverse side 120 is an annular tapered, or frustoconical surface 138, the widest diameter of the cone opening toward the obverse side 120 of the plate. The taper of the frustoconical surface 138 may preferably range from 1 to 7 degrees so that the taper is self-locking. More specifically, the taper may range from 2 to 5 degrees. Yet more specifically the taper may be 3 degrees. When a spherical surface of a pad 106 is compressed against the frustoconical surface 138 at a selected level of force, an interference taper mechanical lock is provided between the pad 106 and the plate 102. In other embodiments of the invention, surface 138 could be spherical, or flat. Each frustoconical surface 138 and surrounding plate body may also be termed a conical socket 139.

A second aperture or bore 140 extends through the plate body 118 from the obverse side 120 to the reverse side 122. A portion of the bore 140 is bounded by a frustoconical bore surface 142, the widest diameter of the cone opening toward the reverse side 122. A rim surface 144 surrounds the remainder of the bore adjacent the reverse side of the plate, and may be smaller in diameter than the widest diameter of the frustoconical bore surface. The rim surface 144 may also be smaller in diameter than a portion of the collet 112. Bore 140 is tapered, sized and shaped to retain a portion of the collet 112 when the locking mechanism is actuated to lock the plates 102, 104 together. Bore 140 may be a polyaxial connection feature, and with collet 112 may form a polyaxial connection wherein plate 102 is polyaxially rotatable relative to the locking mechanism prior to actuating the locking mechanism to lock out further movement between the plate and the locking mechanism. Bore 140 further includes a rotation axis 146 about which plate 102 is polyaxially rotatable prior to lock out, the bore centered about the rotation axis.

At least one instrument connection feature, or element 150, may be formed on plate 102 to provide a site for connection to insertion, compression, and/or locking instrumentation. Connection element 150 may be generally annular and may include an opening 152 which is situated in a spherical socket or cup 154. Cup 154 includes a first end toward the reverse side 122 of the plate, a second end toward the obverse side 120 and a middle portion between the first and second ends. The middle portion may be wider than the first end so that the middle portion undercuts the first end. The middle portion may also be wider than the second end. A plurality of tabs 156 protrude from the first end of the cup 154 on the reverse side 122. The tabs 156 may be curved, and each may project slightly toward a center axis 158 of the cup. When a corresponding spherical connection feature on an instrument is advanced into the cup 154, the tabs 156 may elastically deform to grip the instrument spherical connection feature. Cup 154 and the corresponding connection feature of the instrument may have shapes other than spherical, so long as the connection feature fits in the cup 154 and provides a knob end corresponding to the undercut middle portion of the cup 154.

Figure 6A:
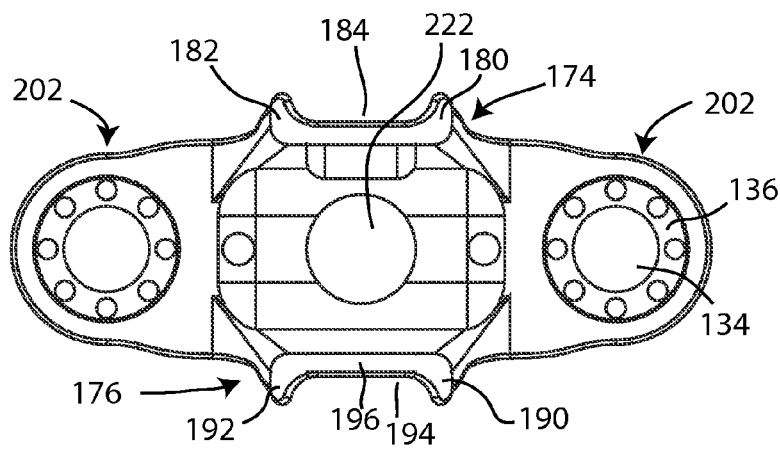
FIG. 6A is a view of an obverse side of the second plate of the spinous process fusion implant of FIG. 1.
Figure 6B:
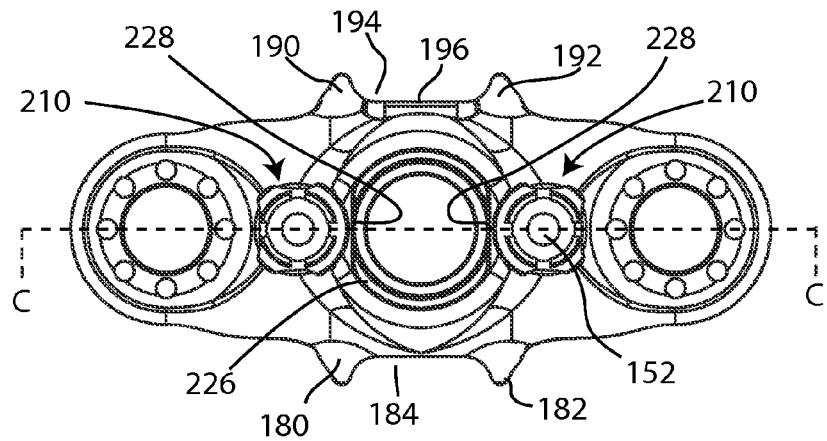
FIG. 6B is a view of a reverse side of the plate of FIG. 6A.
Figure 6C:
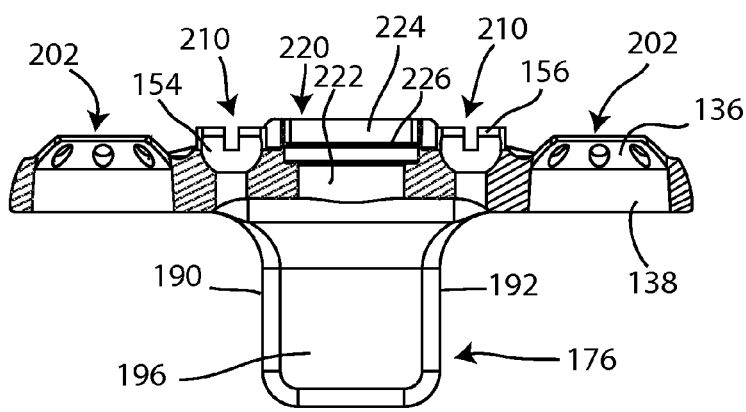
FIG. 6C is a cross-sectional view of the plate of FIG. 6B taken along section line C-C.
Figure 7A:
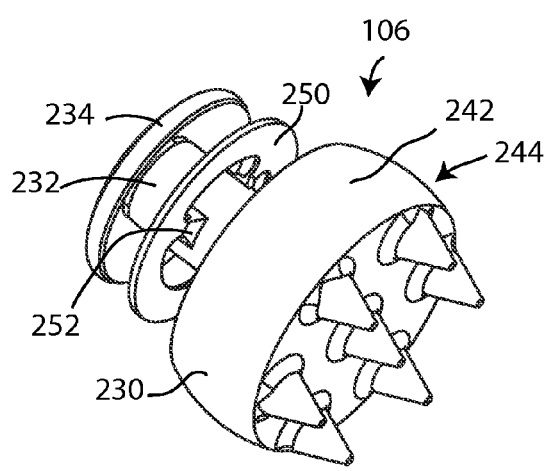
FIG. 7A is an isometric view of a fixation pad of the spinous process fusion implant of FIG. 1.
Figure 7B:
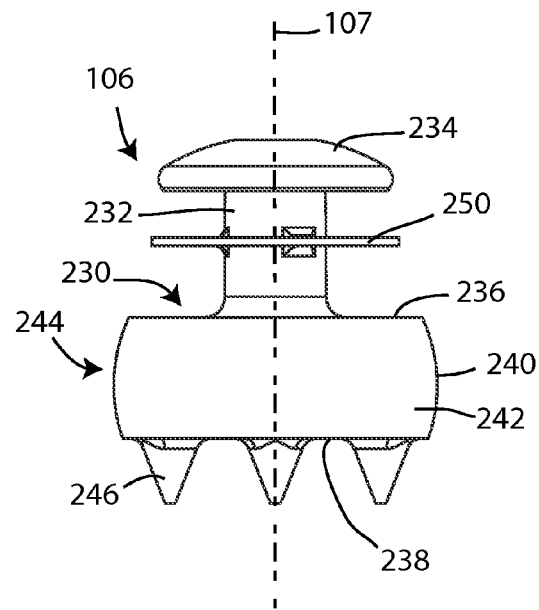
FIG. 7B is a side view of the fixation pad of FIG. 7A.
Figure 7C:
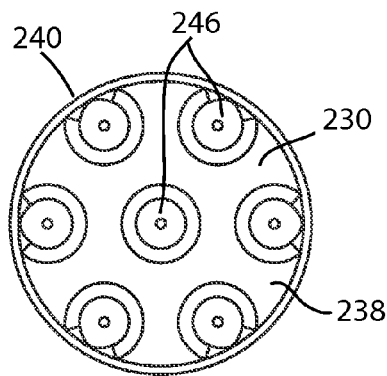
FIG. 7C is a view of a bone-facing end of the fixation pad of FIG. 7A.
Figure 7D:
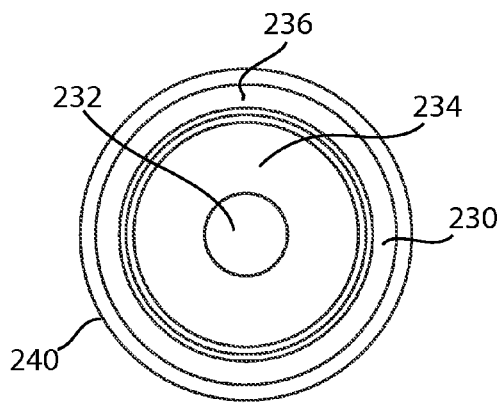
FIG. 7D is a view of an opposite end of the fixation pad of FIG. 7C.

Referring to FIGS. 5A-5C, isometric and side views of the extension plate, or plate 104, are shown. FIG. 6A shows the obverse side of extension plate 104, FIG. 6B shows the reverse side, and FIG. 6C is a cross-sectional view of extension plate 104 taken along line C-C in FIG. 6B.

Extension plate 104, which may be a supporting structure, includes a generally rectangular plate body 160 having a first, or obverse side 162, and a second, or reverse side 164, opposite the obverse side. When implanted according to one embodiment of the invention as shown in FIG. 2, the obverse side 162 is a bone-facing side. Extension plate 104 has a first extension plate edge 166, a second extension plate edge 168, a first extension plate end 170 and a second extension plate end 172. A first wall 174 extends substantially perpendicularly to the plate body 160 from the first extension plate edge 166, and a second wall 176 extends substantially perpendicularly to the plate body 160 from the second extension plate edge 168. First wall 174 includes a window 178. First and second protruding edges 180, 182 project perpendicularly from the first wall 174, forming a first open channel 184 between them.

Similarly, second wall 176 includes first and second protruding edges 190, 192 which project perpendicularly from the second wall, forming a second open channel 194 between them. A wall body 196 spans between the first and second protruding edges. When extension plate 104 is implanted in a portion of a spine as seen in FIG. 2, the protruding edges 190, 192 of the second wall may contact first and second spinous processes, as seen in FIG. 2. The thicker profile of the protruding edges 190, 192 may present more surface area for contact with the spinous processes than would the thinner wall body 196. The thicker protruding edges, providing greater surface area, may be less likely to damage surrounding tissues such as the spinous processes than would a thinner edge presenting less surface area.

Extension plate 104 further includes at least one polyaxial element 202 which may provide for polyaxial connection of a pad 106 to the plate, wherein the pad may be positioned at any of a continuum of positions relative to the plate upon locking attachment to the plate. Each polyaxial element 202, which may be termed a pivot element, may include features identical to those previously set forth for polyaxial element 132 on plate 102, to at least include aperture 134, domed flange 136, and frustoconical surface 138. Similarly, extension plate 104 may further include at least one instrument connection element 210, to provide a site for connection to insertion, compression, and/or locking instrumentation. Each connection element 210 may include features identical to those previously set forth for connection element 150 on plate 102, at least including opening 152, spherical cup 154, and tabs 156.

A pin connection feature 220 which retains a pin or post in a fixed rotational alignment may occupy a central position on extension plate 104. Pin connection feature 220 includes an aperture or bore 222 which extends through the plate from the obverse side to the reverse side, and a counterbore 224 situated at the end of the bore on the reverse side 164 of the plate 104. A protrusion 226 forms a step in the counterbore 224. The bore 222, counterbore 224 and protrusion 226 are generally annular; however one or more flattened portions 228 may be formed on the inner sides of the bore, counterbore, and/or protrusion to prohibit rotation of a pin or post coupled to the plate 104 to extend through the pin connection feature 220.

Referring to FIGS. 7A-D and 8A and 8B, one or more pads 106 may be lockingly coupled to plate 102 and/or extension plate 104. Pad 106 is generally radially symmetrical about a rotation axis 107 and includes a pad body 230, stem 232, and a cap 234. The cap 234 may be formed separately from the pad body and stem, and frictionally or snap fitted onto stem 232 to facilitate assembly of the pad with the plate. Cap 234 may function as a retaining feature, preventing unintentional disassembly of the pad from the plate once assembled together as in FIGS. 8A and 8B. Pad body 230 may be integrally formed with stem 232, and includes a first side 236, a second side opposite the first side comprising a bearing face 238, and a spherical wall 240 extending between the first side and the bearing face. The exterior of the spherical wall 240 is an annular bearing surface 242 which is inherently spherical, as it provides the exterior of the spherical wall. The outer diameter of the first side 236 may be less than the outer diameter of the bearing face 238 as in FIG. 7B; in other embodiments the outer diameters may be equal. The major diameter of the spherical wall 240 is greater than the outer diameters of the first side 236 and the bearing face 238. The spherical wall 240 and its surface 242 form a polyaxial feature 244 for locking with a polyaxial element, including polyaxial elements 132, 202 of plates 102, 104. The polyaxial feature may also be termed a pivot feature as it allows the pad to pivot and/or rotate relative to a pivot element. On the bearing face 238, a plurality of protrusions, or teeth 246 project away from the bearing face. The protrusions and/or bearing face 238 may further include treatments including but not limited to surface roughening, porous coating, knurling, and other treatments to enhance engagement with bony structures. In other embodiments of the invention, the protrusions may include spikes, barbs, pins, prongs, teeth, ridges, tines, pegs, and knurling, among others. In the embodiment shown the teeth 246 are advantageously sized to engage the cortical bone of the spinous process without penetrating cancellous bone, when implanted. In other embodiments of the invention, a pad 106 may not include any teeth or protrusions but instead have a relatively smooth bearing face 238.

Encircling the stem 232 between the pad body 230 and the cap 234 is a thin, generally flat spacer 250. Spacer 250 is joined to stem 232 by at least one stalk 252, and can prevent unintentional locking between the polyaxial feature of the pad 106 and a plate 102, 104. The spacer 250 is deflectable relative to the pad body 230 and stem 232 under a relatively low spacer deflecting force. The spacer 250 may break free of the stem 232 if a sufficient force is applied to it to break the stalks 252.

Figure 8A:
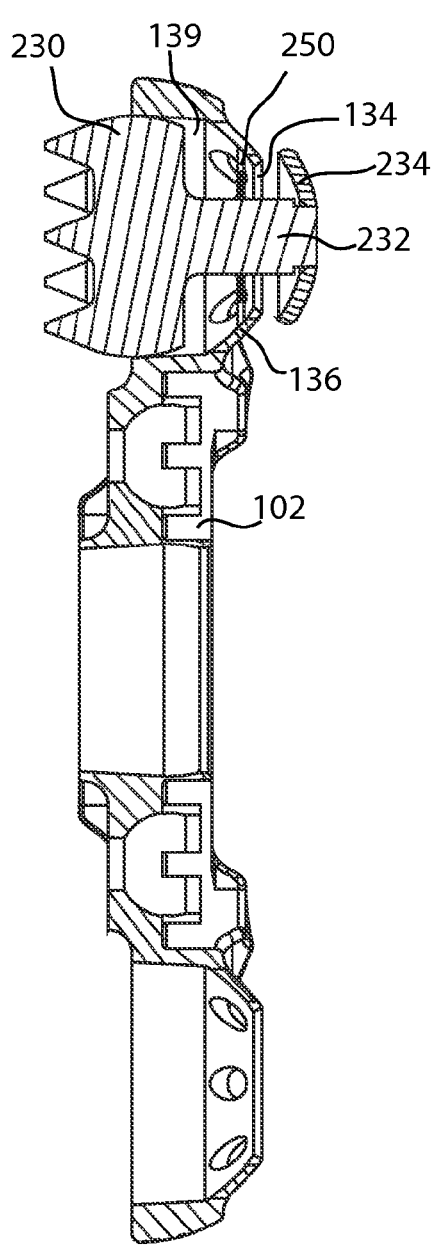
FIG. 8A is a cross-sectional side view of the first plate of the spinous process fusion implant of FIG. 1 with a fixation pad in an unlocked configuration.
Figure 8B:
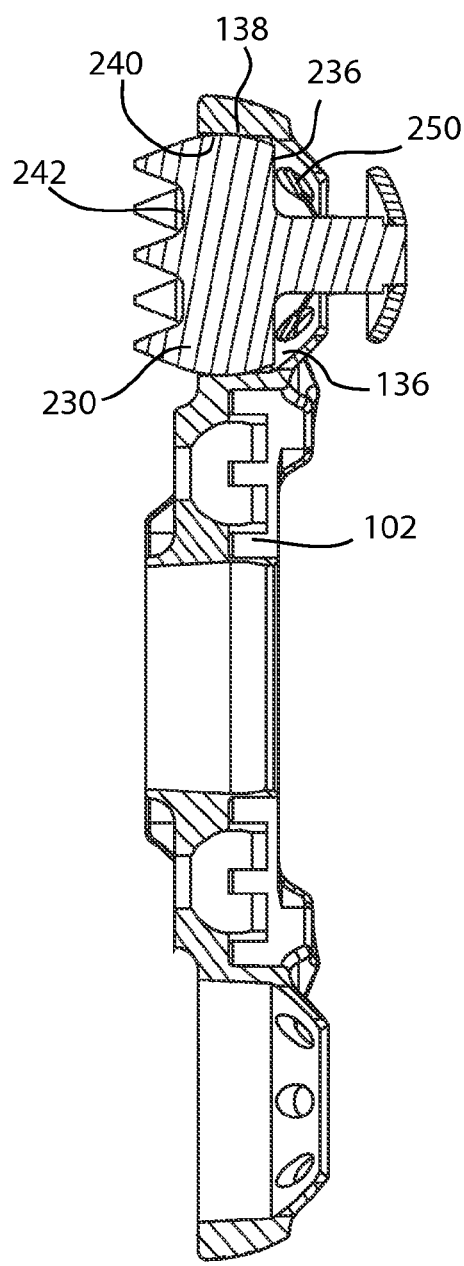
FIG. 8B is a cross-sectional side view of the plate and pad of FIG. 8B with the fixation pad in a locked configuration.
Figures 9A, 9B:
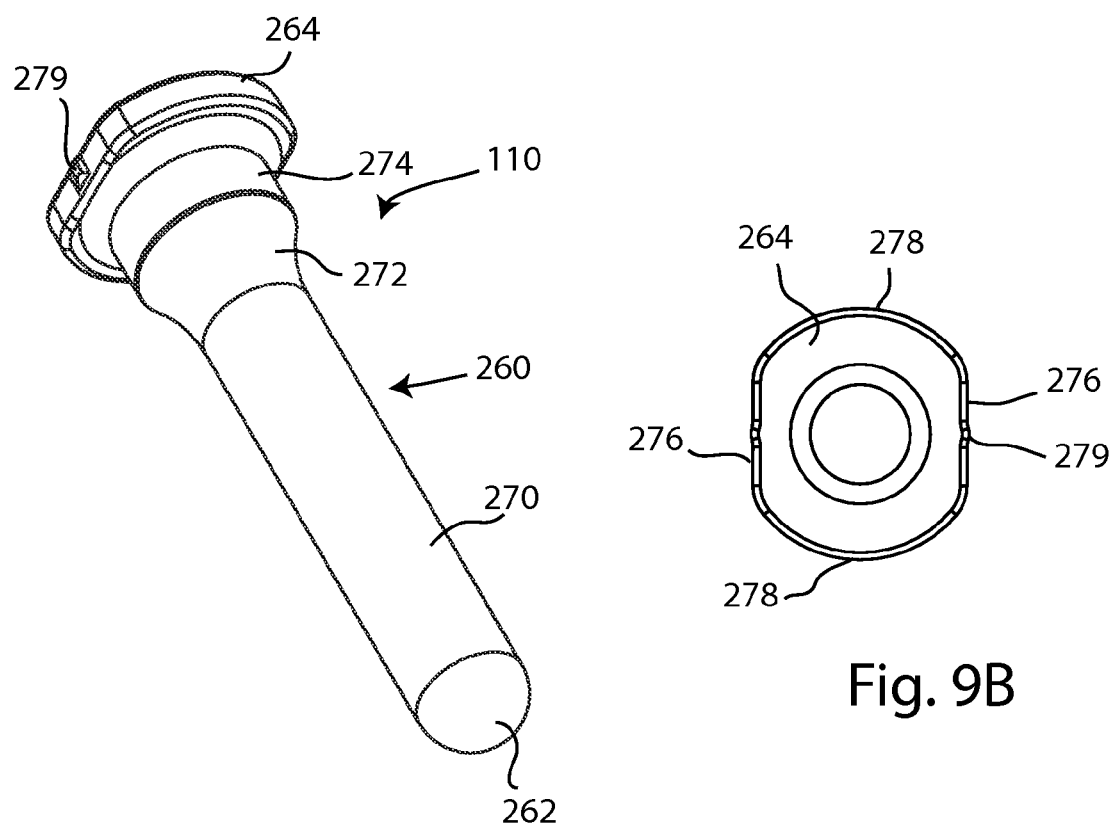
FIG. 9A is an isometric view of a post of the locking mechanism of the spinous process fusion implant of FIG. 1.
FIG. 9B is an end view of a head of the post of FIG. 9A.

Referring to FIGS. 8A and 8B, a pad 106 is shown captive to a plate 102 in unlocked and locked configurations. In the unlocked configuration shown in FIG. 8A, pad body 230 is partially received within conical socket 139, and stem 232 extends through plate aperture 134. Intact spacer 250 is touching the obverse side of flange 136, which functions as a retainer to retain the pad and prevent unintentional disassembly of the plate from the pad. In this configuration, pad 106 can pivotably and/or rotationally move within conical socket 139 relative to plate 102. However, with the spacer touching the obverse side of the flange, the pad body 230 is held spaced apart from conical socket 139 to prevent unintentional or premature locking between the pad and the plate. The spacer must deform or break in order to position the pad body for locking with the conical socket 139. This arrangement permits the pad to automatically adjust its orientation so that bearing face 238 is aligned with a bone surface before the pad is locked to the plate. In FIG. 8B, pad 106 is in a locked configuration relative to plate 102. Pad body 230 is captured within conical socket 139, with spherical wall 240 in a wedged relationship or frictional lock with frustoconical surface 138, and first side 236 relatively closer to the domed flange 136. Spacer 250 has been deflected toward pad body 230 and is captured between flange 136 and the pad body. In FIG. 8B, pad 106 is shown in a neutral or unrotated position relative to plate 102 in which the first side 236 and bearing face 238 are generally parallel to the obverse side of the plate and axis 107 is generally perpendicular to the obverse side of the plate; however pad 106 could also in a tilted or rotated position relative to plate 102 in the locked configuration, as seen in at least FIG. 2. Pad 106 may also be neutral or tilted relative to the plate while in the unlocked configuration. When in a tilted position relative to the plate, the bearing face 238 may be oblique to the obverse side, as demonstrated in FIG. 2. It is appreciated that one plate 102 may be locked with one or more pads 106, each pad in an independent rotational position relative to the plate. Similarly, extension plate 104 may be locked with one or more pads 106, each pad in an independent rotational position relative to the plate.

A locking mechanism may advantageously lock plates 102 and 104 together in a plate assembly. Referring to FIGS. 1 and 9-11, an embodiment of a locking mechanism 108 may include the pin or post 110, collet 112, and ring 114. As seen at least in FIG. 9A, post 110 includes a shaft 260 extending between a first end 262 and a second end which includes a head 264. First end 262 may be rounded, which may prevent cutting or damage to body tissue in the adjacent environment when implanted. Shaft 260 may further include a straight portion 270, a shoulder 272, and a collar 274 disposed between the straight portion and the head 264, the shoulder providing an increase in shaft diameter between the straight portion 270 and the collar 274. The post head 264 is generally circular; however two straight, or flattened sections 276 are disposed on opposite sides of the head interspersed by two rounded sections 278. The engagement of flattened sections 276 with flattened portions 228 when post 110 is coupled with extension plate 104 prevents rotation of post 110 relative to the plate. Additionally, at least one protrusion 279 on the post head 264 frictionally engages the counterbore 224 to rigidly connect the post with the extension plate 104 and prevent rotation. On another embodiment of the invention, the protrusion may be located on the counterbore and engage the post head for connection and/or prevention of rotation. The protrusion may alternately be formed on the head 264, collar 274, shoulder 272, or shaft 260 of the post 110 or on the flattened portions 228 or bore 222 of pin connection feature 220. On yet other embodiments, other features providing a rotation resistant coupling between the post and the plate may be present. One example of a rotation resistant coupling is the coupling between a driver tip and a screw head, of which many are known in the art. Others include keyways, snap fittings, tongue in groove fittings and any other rotation resisting couplings known in the art.

Figure 10A:
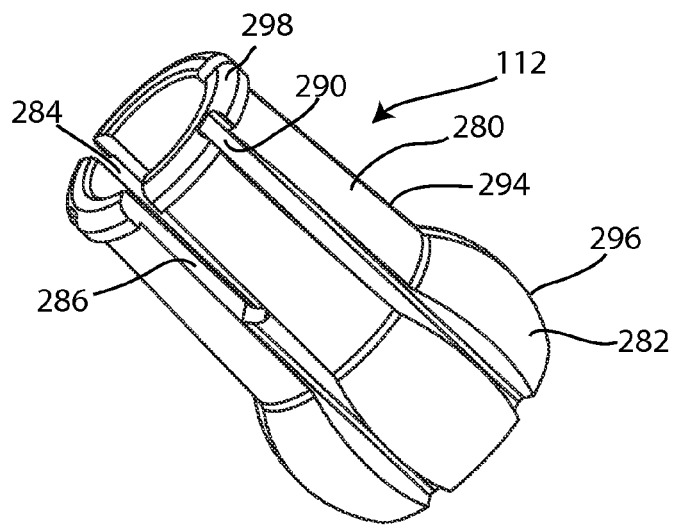
FIG. 10A is an isometric view of a collet of the locking mechanism of the spinous process fusion implant of FIG. 1.
Figure 10B:
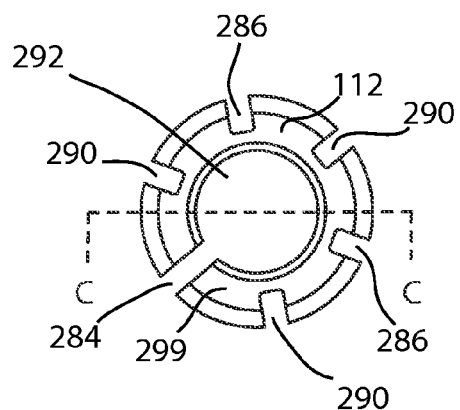
FIG. 10B is an end view of a first end of the collet of FIG. 10A.
Figure 10C:
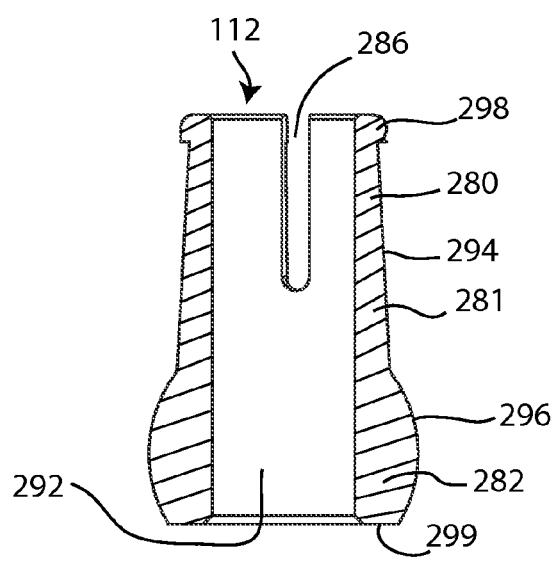
FIG. 10C is a cross-sectional side view of the collet of FIG. 10B taken along section line C-C.

Referring to FIGS. 10A-10C, collet 112 includes a collet body 281 having a frustoconical shaft portion 280 and a sphere portion 282. The collet 112 is split, having a longitudinal gap 284 extending the entire length of the collet and radially through the collet body, and at least one partial gap 286 extending through the collet body partially along the length of the collet. The longitudinal gap provides flexibility to the collet. The partial gap may selectively increase the flexibility of the collet in the vicinity of the partial gap. A plurality of grooves 290 also extend longitudinally along the length of the collet, but do not extend radially through the collet body 281. The grooves may selectively increase the flexibility of the collet in the vicinity of the grooves, but to a lesser degree than that provided by the partial gap. The collet 112 has a neutral state in which it is relaxed, or undeformed, as seen in FIGS. 10A-10C. In this state, a central bore 292 of the collet has a constant diameter. When acted upon by a force from the inside such as a post in the central bore or a force from the outside such as a ring encircling the collet, the collet may deform and the diameter of the central bore may increase or decrease. The outer surface of the shaft portion is a collet frustoconical surface 294, and the outer surface of the sphere portion 282 is a collet spherical surface 296. The taper of the frustoconical surface 294 may preferably range from 1 to 7 degrees so that the taper is self-locking. More specifically, the taper may range from 2 to 5 degrees. Yet more specifically the taper may be 3 degrees. When the collet is assembled with the plate 102, the rim surface 144 of the plate may engage with the sphere portion 282 to retain collet 112 within bore 140. A collet lip 298 forms one end of the collet adjacent the shaft portion 280. An opposite end of the collet 112 may include a collet flat end 299.

Figure 11A:
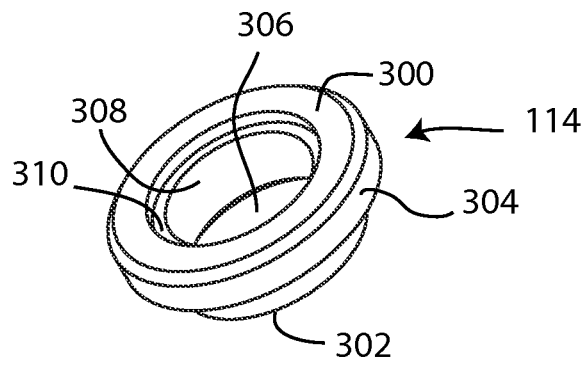
FIG. 11A is an isometric view of a locking ring of the locking mechanism of the spinous process fusion implant of FIG. 1.
Figure 11B:
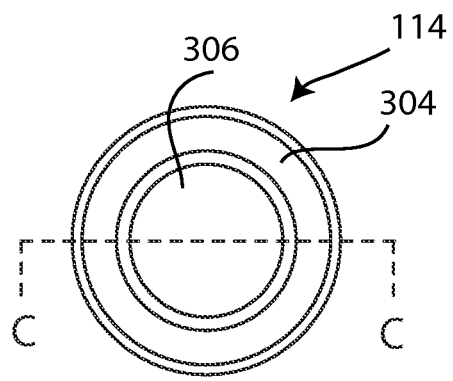
FIG. 11B is an end view of a first end of the ring of FIG. 11A.
Figure 11C:
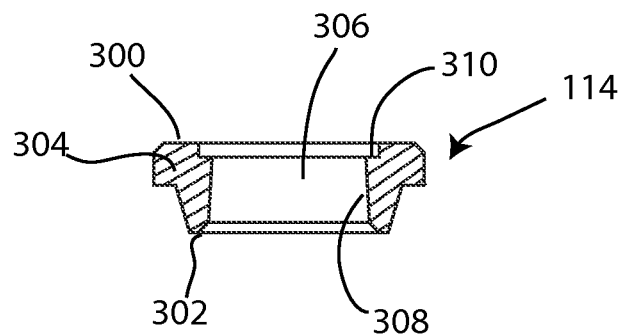
FIG. 11C is a cross-sectional side view of the ring of FIG. 11B taken along section line C-C.

Referring to FIGS. 11A-11C, ring 114 is annular, having a first end 300 and a second end 302. A ring body 304 extends between the two ends, and a ring bore 306 extends through the ring body 304 between the first and second ends. A frustoconical bore wall 308 bounds the bore. A taper or angle of the frustoconical bore wall 308 may be the same as a taper or angle of the collet frustoconical surface 294. The taper of the frustoconical bore wall 308 may preferably range from 1 to 7 degrees so that the taper is self-locking. More specifically, the taper may range from 2 to 5 degrees. Yet more specifically the taper may be 3 degrees. An annular step 310 is adjacent the ring bore 306 at the first end 300. When the ring 114 is assembled with the collet 112, the collet lip 298 may engage with the step 310 to retain ring 114 about the collet 112.

In one embodiment, spinal implant 100 may be provided entirely pre-assembled, with pads 106 in an unlocked configuration and the locking mechanism also unlocked, as seen in FIG. 1. In another embodiment, the implant may be provided in two pre-assembled combinations. In the first combination, plate 102 is assembled with two pads 106 captive to the plate, the intact spacers 250 preventing premature locking of the pads to the plates. Collet 112 is captured in bore 140, but not locked, and ring 114 is retained on collet 112. In the second combination, extension plate 104 is assembled with two pads 106 captive to the plate, the intact spacers 250 preventing premature locking of the pads to the plates. Post 110 is inserted through bore 222 on extension plate 104. An advantage of providing the implant in the two combinations is that different length posts 110 may be substituted intraoperatively as desired to match patient anatomy.

Figure 12:
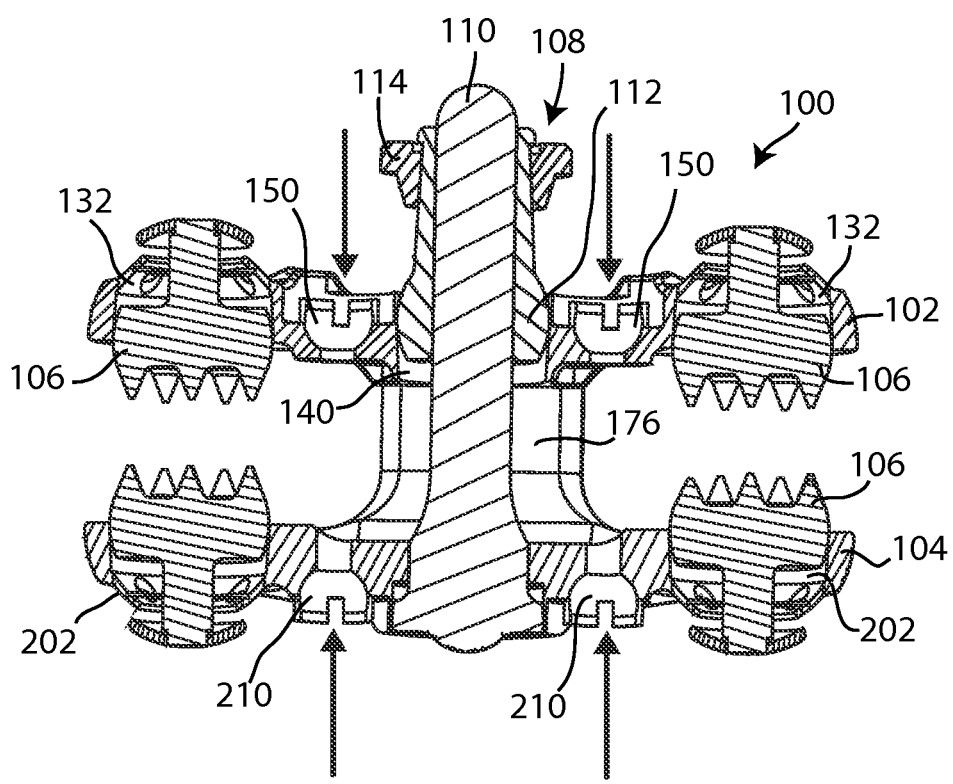
FIG. 12 is a cross-sectional side view of the spinous process fusion implant of FIG. 1 with the fixation pads and locking mechanism in unlocked configurations.
Figure 13:
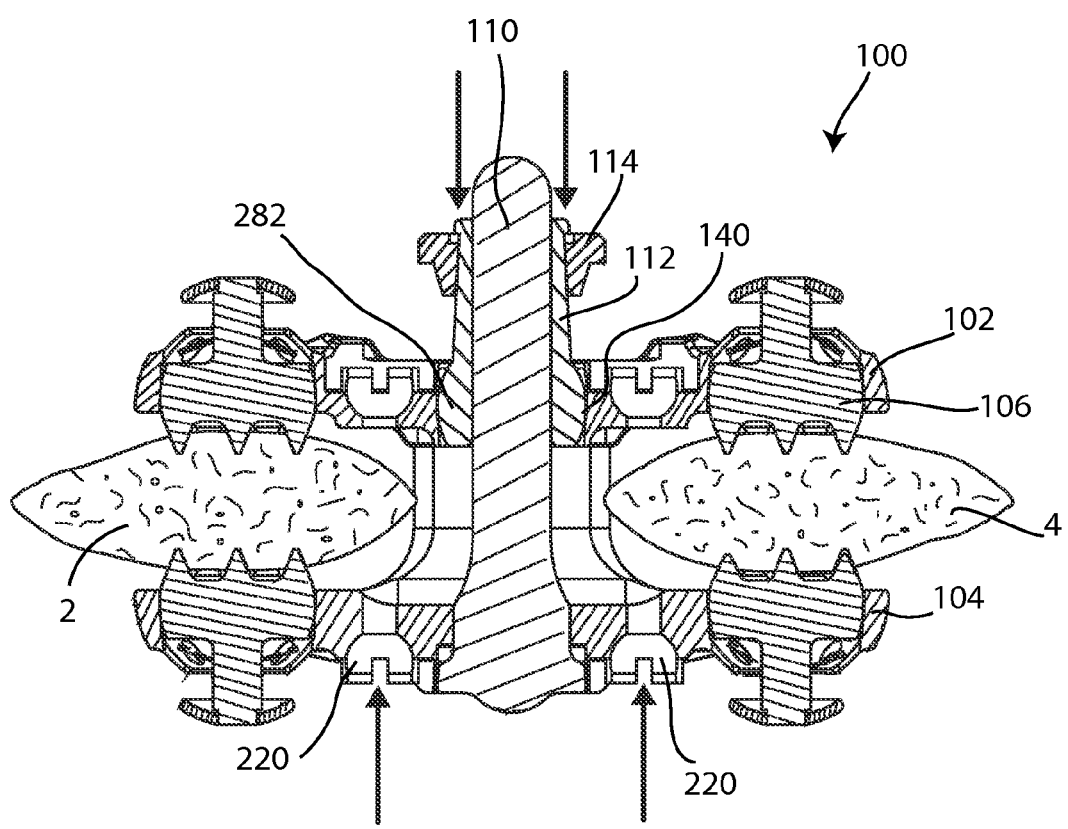
FIG. 13 is a cross-sectional side view of the spinous process fusion implant of FIG. 1 with the fixation pads in a locked configuration and the locking mechanism in a provisionally locked configuration.
Figure 14:
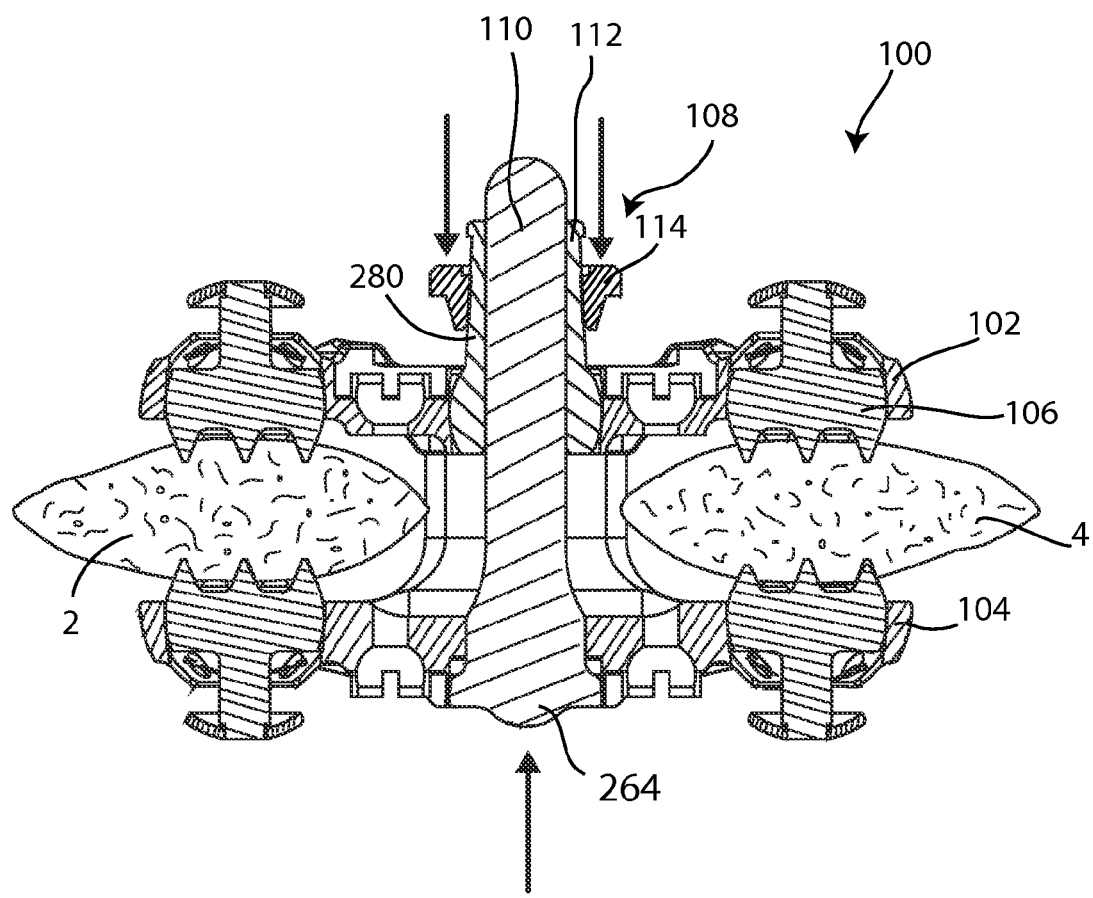
FIG. 14 is a cross-sectional side view of the spinous process fusion implant of FIG. 1 with the fixation pads in a locked configuration and the locking mechanism in a locked configuration.

Referring to FIGS. 12-14, an assembled spinal implant 100 includes plate 102, extension plate 104, a plurality of pads 106, and the locking mechanism 108. FIG. 12 shows a cross-sectional view of implant 100 in an unlocked configuration. In this configuration, a pad 106 is received in each plate polyaxial element 132, 202, but the pads are not yet frictionally locked with the plates. Similarly, collet 112 is received in bore 140, but is not yet frictionally locked within the bore. It is appreciated that although plate 102 is depicted as generally parallel to extension plate 104, the polyaxial connection including sphere portion 282 and bore 140 allows for polyaxial rotation, or tilting, of plate 102 relative to the locking mechanism 108 and extension plate 104. Plate 102, collet 112 and ring 114 may also translate relative to extension plate 104 in the unlocked configuration. Similarly, each pad 106 can polyaxially rotate or tilt relative to its corresponding polyaxial element 132, 202. This polyaxiality allows for individualized fit of each of the pads 106 against the lateral surfaces of the spinous processes, and of the plates 102, 104 relative to one another and the spinous processes. By way of non-limiting example, if the medial-lateral widths of the spinous processes vary from one another, plate 102 can tilt and be locked in the tilted orientation to provide an individualized fit to the spinous process anatomy. In the same way, the bearing faces of the individual pads 106 can advantageously tilt to fit the contour of the specific bony structure, or spinous process surface. This may be advantageous over systems with fixed position plates and/or bearing faces by conforming to the natural contours of the bony structures, potentially providing a more conforming fit, reduced implant prominence and reduced interaction or interference with the adjacent body environment. It can be appreciated that, in the final implanted position, plate 104 may be tilted with respect to standard medical planes of reference in order to provide a conforming fit against the spinous processes or other bony surface. However, in the limited context of the spinal implant 100, plate 104 is fixed with respect to the post 110 and thus serves as a frame of reference for movable portions of the spinal implant.

Referring to FIG. 12, the arrows show an initial compression, or pad locking force which, when applied, compresses the two plates 102, 104 together. When the implant 100 is positioned as shown in FIG. 2 with plates 102 and 104 on opposite sides of spinous processes, this compression presses the plates 102, 104 medially toward the spinous processes and seats the pads into the bone of the spinous processes. Initially, when the compression force is low, the plate 102 body and pads are free to rotate in order to align properly to the bone, but as the load is increased, the pads are rigidly and permanently locked to the plate via a spherical taper lock. This initial compression force may be applied gradually by a compression instrument which engages in instrument connection elements 150, 210. As the compression force increases, a spacer deflecting level of force may be reached, followed by a pad locking level of force greater than the spacer deflecting force. In a preferred embodiment, the pad locking level of force may be calibrated so that the pads lock to the plate after the protrusions 246 have sunk into the bone surface, but before the complete bearing faces 238 have indented, or crushed, the bone surface. In other words, the protrusion seating force is lower than the pad locking force, which is lower than the indentation, or crushing force.

Referring to FIG. 13, a cross-sectional view is shown of implant 100 inserted between two spinous processes 2, 4. The initial compression force described with reference to FIG. 12 has been applied, and the pads 106 are wedged, or taper locked, to the plates 102, 104 and seated in the spinous processes 2, 4. In addition, a first locking compression force indicated by the arrows in FIG. 13 has also been applied to press the spherical collet 112 into the tapered bore 140 of the plate body 118. This action wedges the sphere portion 282 of the collet between the bore 140 and the post 110, which locks out the plate polyaxiality and thereby the position of the plate 102. This action also secures the spherical collet 112 to the post 110 to maintain the initial compression between the two opposing plates and the spinous processes. This compressive first locking, or provisional locking force may be applied by a locking instrument which engages the instrument connection elements 210 on extension plate 104, and the collet 112.

Referring to FIG. 14, a cross sectional view shows spinal implant 100 in a second, or final locked configuration. In this second locked configuration, the force indicated by the arrows in FIG. 14 has been applied between post head 264 and the locking ring 114. This final or second locking compression force presses the locking ring 114 along the conical taper of the spherical collet 112, further securing the collet to the post 110. The frustoconical shaft portion 280 of the collet is wedged between the ring 114 and the post 110. This step also advantageously isolates the compression force to the tapered locking mechanism 108 so that no additional or unintentional compression is placed on the spinous processes. The plate 102 and collet 112 are now completely rigidly locked into position. At this point, no rotation or relative movement can occur between the two plates, or between the plates and the pads.

In a first embodiment of a method of implantation, the entire implant is assembled in the unlocked configuration as seen in FIGS. 1 and 12. The implant, biased in the unlocked configuration, may be connected to an implantation/compression instrument. The instrument may be used to insert the implant between two spinous processes, and pad and plate lockout are carried out as described previously with reference to the description of FIGS. 12-14.

In another embodiment, a first combination of plate 102 with captive pads 106 and captive collet 112 and ring 14 may be connected to one instrument. A second combination of extension plate 104 with pads 106 and post 110 may be connected to a separate instrument. The combinations are inserted into the interspinous area separately, and post 110 is inserted into collet 112 in situ to connect the two combinations. Pad and plate lockout are then carried out as described previously with reference to the description of FIGS. 12-14. An advantage of this embodiment is the ability to preserve important soft tissue structures such as the supraspinous ligament.

Prior to or following the implantation process, natural or synthetic bone graft material, a bone block, bone morphogenic protein, and/or other therapeutic agents may be inserted into the chamber 115. These materials may be inserted through window 178, or packed around post 110 before final assembly of the implant.

Implant members according to exemplary embodiments may be manufactured from suitable medical-grade materials, including, but not limited to, titanium and stainless steel, other metals, polymers, or ceramics.

Figure 15:
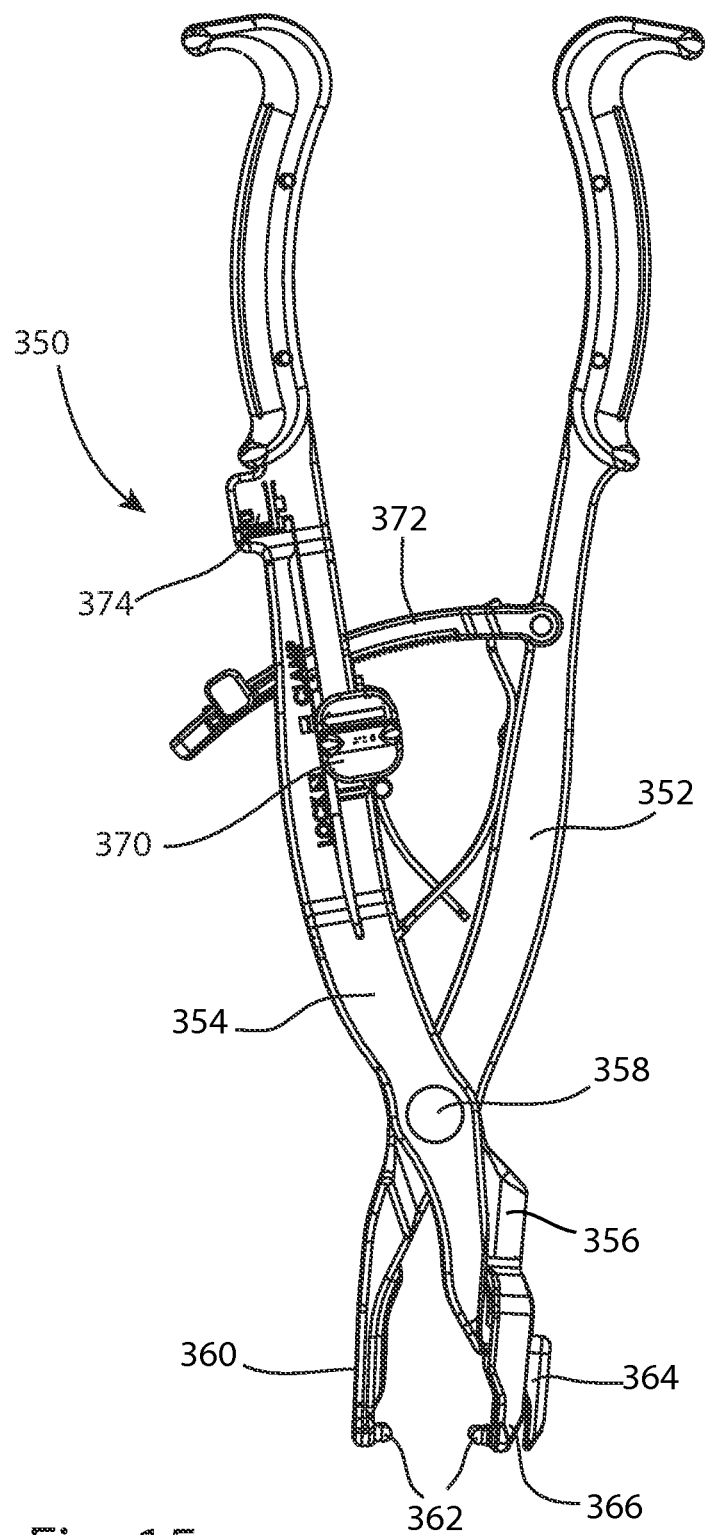
FIG. 15 is a side view of a first instrument for providing insertion, compression and locking.
Figure 16:
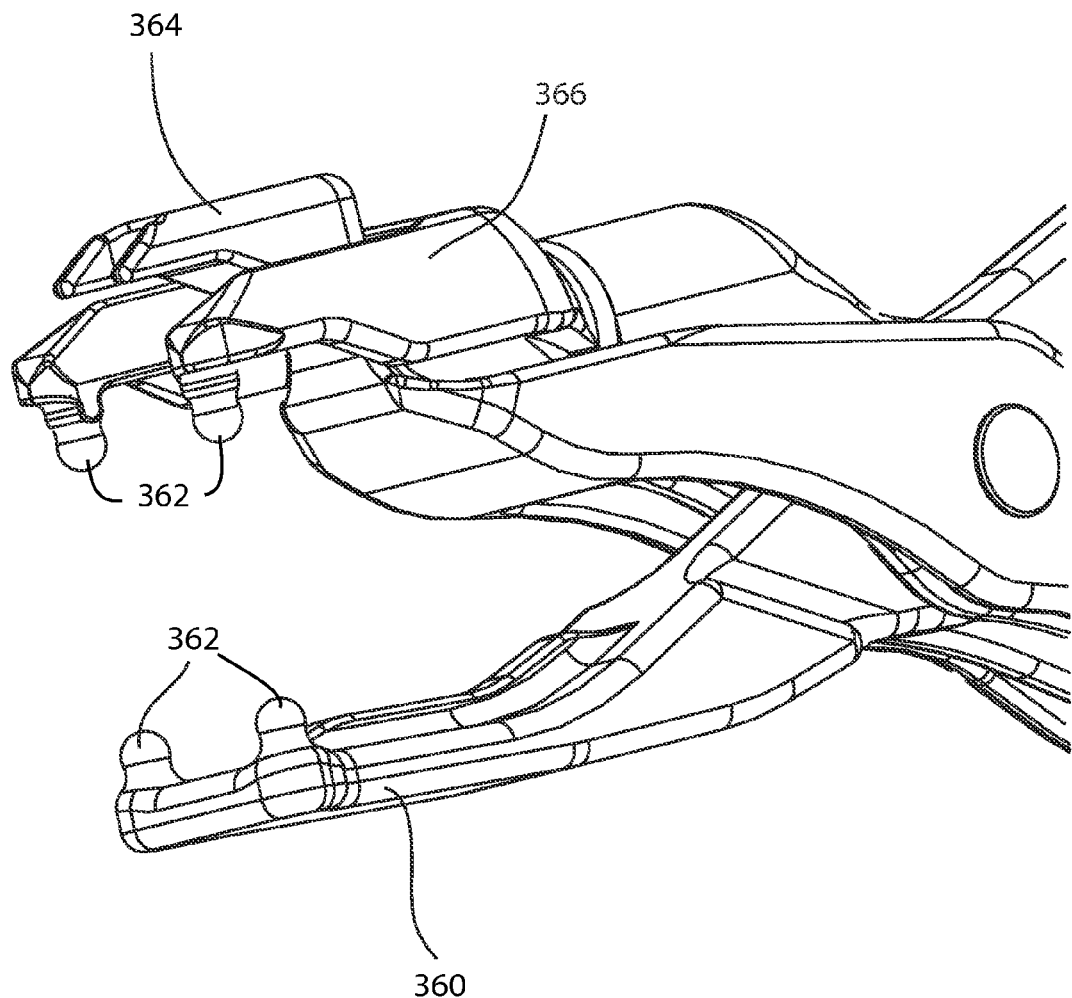
FIG. 16 is an isometric view of a working end of the first instrument of FIG. 15.
Figure 17:
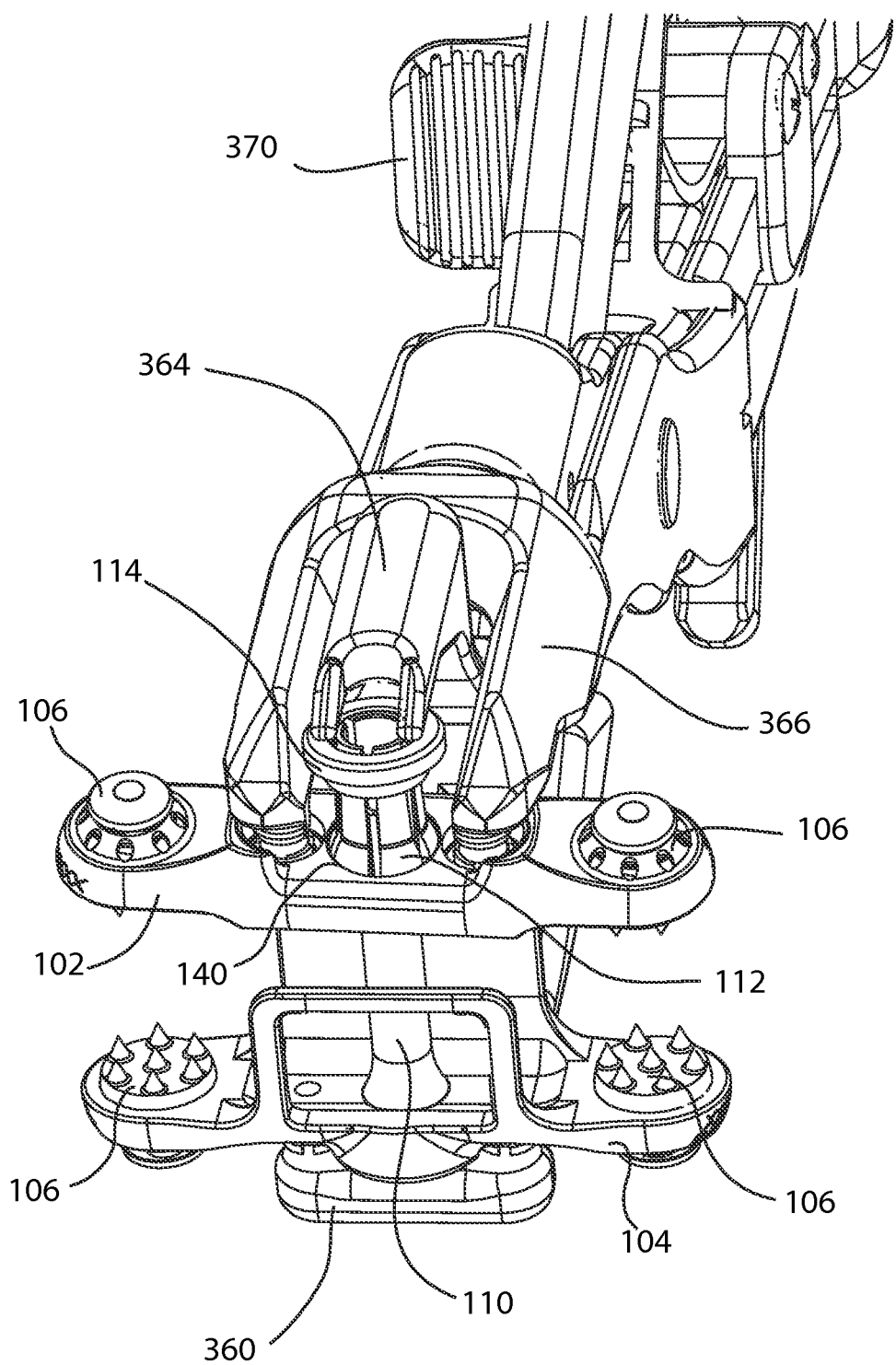
FIG. 17 is an isometric view of the working end of the first instrument of FIG. 16, the instrument holding the spinous process fusion implant of FIG. 1 in an unlocked configuration.

FIGS. 15, 16 and 17 illustrate a first instrument 350 which may be used to provide insertion, compression and locking of spinal implant 100 or other related embodiments. This instrument and its operation are described in detail in U.S. Provisional Patent Application Ser. No. 61/366,755, the entirety of which is incorporated by reference in this document.

First instrument 350 includes a first leg 352, second leg 354 and third leg 356 which are pivotable relative to one another about a pivot point 358. A first leg working end 360 includes spherical tips 362 which may engage instrument connection elements on an implant, such as instrument connection elements 150, 220 on spinal implant 100. A second leg working end 364 is forked, and the fork may be sized to engage a portion of collet 112 on spinal implant 100. A third leg working end 366 also includes spherical tips 362 which may engage instrument connection elements on an implant. Third leg working end 366 is rotatable relative to the first 360 and second 364 working ends, which allows for polyaxial adjustment of spinal implant 100 prior to locking the fixation pads 106 and central locking mechanism 108.

A selector switch 370 is actuable between a first position and a second position. When the selector switch is in the first position and the instrument is actuated by moving the handles toward one another, the second 364 and third 366 leg working ends move together, the third leg working end 366 applying a compressive force in opposition to the first leg working end 360. The third leg working end 364 may rotate or pivot to allow the implant to properly orient itself to the geometry of the bone as the compressive force is applied. The second leg working end 364 remains in a position where it is not applying any compressive force. The compressive force between the first and third legs is maintained by a ratcheting arm 372. When the switch is moved to the second position and the instrument is actuated by moving the handles toward one another, the second 364 and third 366 leg working ends become disengaged. The second leg working end 364 is then free to move independently of the third leg working end 366 and can apply a compressive locking force to a central member 108 of the implant, locking it in place.

As shown in FIG. 17, first instrument 350 may be used to grip implant 100, with spherical tips 362 on the instrument engaging in socket-like cups 154 on plates 102, 104. The first leg working end may be connected to extension plate 104, and third leg working end connected to plate 102. The instrument may be used to lift the implant 100 from packaging or a table, and insert into the interspinous space between the spinous processes. With the selector switch 370 in the first position, the instrument handles may then be compressed together, clamping plates 102, 104 toward one another and the spinous processes as seen in FIG. 12. The third leg working end 366 may pivot to allow pivoting adjustment of plate 102 relative to the spinous processes. Also, plate 102 may translate along post 110 toward extension plate 104. As compression force is applied, a first force level sufficient to deform the spacers 250 may be reached, followed by a second force level, greater than the first force level, sufficient to lock the pads 106 relative to the plates 102, 104. The switch 370 may then be moved to the second position, disengaging the second and third leg working ends from one another. The instrument handles may then be compressed together again, with a locking force now being applied between the extension plate 104 and the collet 112, as seen in FIG. 13. This locking force is isolated so that no additional force is applied between extension plate 104 and plate 102. Collet 112 is wedged into bore 140 of plate 102, locking out movement between the collet 112, post 110, and plate 102. A force indicator 374 may provide an indication such as an audible signal when selected levels of force are reached. Other embodiments of the invention may include other force indicators known in the art including but not limited to markings or stops.

Referring to FIGS. 18A and 18B, a second instrument 380 may be used to move locking ring 114 relative to the collet 112 on spinal implant 100 to provide an additional or final lockout of the locking mechanism 108. Second instrument 380 includes a first leg 382 pivotably connected to a second leg 384. A first leg working end 386 includes a first feature to engage ring 114 of implant 100. In an embodiment, the first feature is an opening 388 sized fit around post 110 and engage ring 114 without engaging collet 112, allowing the instrument to urge the ring 114 to move relative to the collet 112. A second leg instrument working end 390 includes a second feature to engage post 110. In an embodiment, the second feature is a recess 392 sized to receive a portion of post head 264. The instrument 380 may be positioned with spinal implant 100 so that the first leg working end 386 engages the ring 114 and the second leg working end 390 engages the post 110. The handles may be moved toward one another to provide a force to move ring 114 along collet 112, further locking the locking mechanism 108, as seen in FIG. 14. A force indicator 394 may provide an indication such as an audible signal when a selected level of force is reached.

It is appreciated that in alternate embodiments of the invention, the features and capabilities of the first 350 and second 380 instruments may be combined on a single instrument, or found on separate instruments. For example, a first instrument may provide force for locking of polyaxial pads or feet of an implant, a second instrument may provide force for a provisional lock of a locking mechanism, while a third instrument may provide force for a final lockout of a locking mechanism. It is also appreciated that first 350 and second 380 instruments may be used for providing insertion, compression and/or locking of other plate systems, implants or locking mechanisms.

The individual components above may be provided separately or in combinations or kits. The implant may be provided in a variety of sizes to allow a practitioner to select a size appropriate for the patient's anatomy and/or desired outcome. Any component may vary in overall size or selected individual dimension. For example, the post, ring and/or collet may each be available in a variety of lengths and/or radii. The plates may be available in a variety of lengths and widths, and with varying numbers of polyaxial connection features. The instruments may be individually sized to fit a particular plate size, or may be available in a 'one size fits all' configuration in which one instrument can connect with any size plate due to the strategic placement of instrument connection features on the plates. An embodiment of a kit may include an implant and instrumentation for implantation, compression, and locking. Another embodiment of a kit may include only implants in a variety of sizes, and another embodiment may include only instrumentation.

It should be understood that the present system, kits, apparatuses, and methods are not intended to be limited to the particular forms disclosed. Rather, they are to cover all modifications, equivalents, and alternatives falling within the scope of the claims.

The claims are not to be interpreted as including means-plus- or step-plus-function limitations, unless such a limitation is explicitly recited in a given claim using the phrase(s) "means for" or "step for," respectively.

In the foregoing Detailed Description, various features are grouped together in several embodiments for the purpose of streamlining the disclosure. This method of disclosure is not to be interpreted as reflecting an intention that the embodiments of the invention require more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separate embodiment.

The present invention may be embodied in other specific forms without departing from its spirit or essential characteristics. It is appreciated that various features of the above-described examples can be mixed and matched to form a variety of other alternatives. As such, the described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. A bone plate assembly, comprising:
   a first plate, wherein the first plate comprises an obverse side, a reverse side, and a first pivot element configured to allow the plate to pivot about an axis, wherein the reverse side is opposite the obverse side;
   a second plate comprising an obverse side and a reverse side, wherein the reverse side is opposite the obverse side;
   a locking mechanism disposed between the first and second plates, said locking mechanism defining a longitudinal axis; and
   at least one pad carried by the first plate and disposed along the first plate at an offset location with respect to the longitudinal axis, wherein the pad comprises a bearing face including a plurality of protrusions configured to contact a bone and a pad pivot element, wherein the bearing face is adjacent the obverse side, wherein the pad pivot element is configured to allow the at least one pad to pivot about at least one axis relative to the first plate, and wherein the pad pivot element is configured to lock into a fixed position upon receiving a compressive force between the first plate and a bone surface.

2. The plate assembly of claim 1,
   wherein the at least one pad rotates relative to the plate through a range of motion;
   wherein the range of motion comprises a neutral position and a tilted position;
   wherein the bearing face is parallel to the obverse side in the neutral position;
   wherein the bearing face is oblique to the obverse side in the tilted position.

3. The plate assembly of claim 1, comprising:
   an initial configuration, wherein the at least one pad freely rotates relative to the first plate; and
   a final configuration, wherein the at least one pad is locked to the first plate.

4. The plate assembly of claim 3, comprising:
   a spacer, wherein, in the initial configuration, the spacer prevents unintentional locking of the at least one pad to the plate; wherein, in the final configuration, the spacer permits intentional locking of the at least one pad to the plate.

5. The plate assembly of claim 4, wherein the spacer comprises a flange on the at least one pad.

6. The plate assembly of claim 4, wherein, in the initial configuration, the spacer holds a pivot feature spaced apart from the pad pivot element; wherein, in the final configuration, the spacer deforms as the pivot feature is urged against the pad pivot element.

7. The plate assembly of claim 4,
   wherein the at least one pad is urged into position for locking with the plate when a spacer deflecting force is applied to the at least one pad;
   wherein the at least one pad locks with the first plate when a pad locking force is applied to the pad;
   wherein the at least one pad locking force is greater than the spacer deflecting force.

8. The plate assembly of claim 1, wherein the at least one pad is captive to the first plate.

9. The plate assembly of claim 8, comprising:
a retainer, wherein the retainer keeps the at least one pad coupled to the first plate.

10. The plate assembly of claim 9,
wherein the first plate comprises an aperture;
wherein the retainer comprises a cap on the at least one pad, wherein the cap is spaced apart from the bearing face;
wherein the at least one pad extends through the aperture so that the aperture is between the bearing face and the cap;
wherein the aperture is smaller than the bearing face and the cap.

11. The plate assembly of claim 1, comprising a plurality of pads disposed along the first plate at an offset location with respect to the longitudinal axis, each of said plurality of pads configured to rotate polyaxially within an inner surface of the first plate.

12. The bone plate assembly of claim 1 wherein the first pivot element is configured so as to allow the plate to polyaxially rotate relative to a second plate.

13. A plate assembly for attachment to a bone surface, comprising:
a first plate comprising a first obverse side and a first reverse side opposite the first obverse side, said first plate comprising a first pad and a second pad including a plurality of protrusions configured to contact a bone surface;
a second plate comprising a second obverse side and a second reverse side opposite the second obverse side, said second plate comprising a third pad and a fourth pad including a plurality of protrusions configured to contact a bone surface, said first and second plates configured to cooperatively clamp a first and second spinous process; and
a locking mechanism coupling the first plate to the second plate so that the first obverse side faces the second obverse side, said locking mechanism configured to extend longitudinally between the first obverse side of the first plate and the second obverse side of the second plate in the gap formed between the first and second spinous processes;
wherein the plate assembly has an unlocked configuration and a first locked configuration;
wherein, in the unlocked configuration, the first plate rotates and translates relative to the second plate to align the first plate to the bone surface;
wherein, in the first locked configuration, the first plate is rotationally and translationally fixed relative to the second plate;
wherein the plate assembly is configured to transition from the unlocked configuration to the first locked configuration in response to a compression force exerted medially on the first and second plates toward the bone surface, said compression force urging the first obverse side toward the second obverse side and providing an interference lock.

14. The plate assembly of claim 13, wherein, in the unlocked configuration, the first plate polyaxially rotates relative to the second plate.

15. The plate assembly of claim 13, wherein, in the unlocked configuration, the first plate polyaxially rotates relative to the locking mechanism.

16. The plate assembly of claim 15, wherein the first plate comprises a conical socket; wherein the locking mechanism comprises a spherical protrusion; wherein, in the unlocked configuration, the conical socket rotates polyaxially on the spherical protrusion.

17. The plate assembly of claim 13,
wherein, in the unlocked configuration, the first plate and the locking mechanism translate relative to the second plate.

18. The plate assembly of claim 17, comprising:
a post coupled to the second plate in a fixed rotational alignment, wherein the post extends generally perpendicular to the obverse side of the second plate;
wherein, in the unlocked configuration, the first plate and the locking mechanism translate along the post.

19. The plate assembly of claim 13,
wherein, in the first locked configuration, the first plate is rotationally and translationally fixed to the locking mechanism.

20. The plate assembly of claim 13, comprising:
a post secured to the second plate in a fixed rotational alignment, wherein the post extends generally perpendicular to the obverse side of the second plate;
wherein the first plate comprises a conical socket, wherein the post extends through the socket;
wherein the locking mechanism comprises a collet, wherein the collet comprises a spherical protrusion, wherein the post extends through the collet;
wherein, in the first locked configuration, the spherical protrusion is wedged between the conical socket and the post.

21. The plate assembly of claim 20, wherein the post comprises a protrusion, wherein the protrusion frictionally engages the second plate to retain the post on the second plate.

22. The plate assembly of claim 20, wherein the locking mechanism comprises a ring;
wherein the collet comprises a frustoconical shaft adjoining the spherical protrusion, wherein the frustoconical shaft extends through the ring;
wherein the plate assembly has a second locked configuration;
wherein, in the second locked configuration, the frustoconical shaft is wedged between the ring and the post.

23. The plate assembly of claim 22, wherein the frustoconical shaft comprises a partial length longitudinal gap.

24. The plate assembly of claim 13, comprising:
a first wall extending between the first and second plates, wherein the first wall is generally perpendicular to a selected one of the first and second obverse sides, wherein the first wall is contiguous with a first edge of the selected obverse side; wherein the first wall terminates in a first free end adjacent to the other one of the first and second plates.

25. The plate assembly of claim 24, comprising:
a second wall similar to the first wall, wherein the second wall extends between the first and second plates, wherein the second wall is generally perpendicular to the selected obverse side, wherein the second wall is contiguous with a second edge of the selected obverse side opposite the first edge, wherein the second wall terminates in a second free end adjacent to the to the other one of the first and second plates.

26. The plate assembly of claim 24, wherein the first wall further comprises a pair of opposing edges, wherein each one of the pair of edges protrudes from a lateral aspect of the first wall so as to form an open channel extending from the edge of the selected obverse side to the free end.

27. The plate assembly of claim 24, wherein the first wall comprises a window.

28. The bone plate assembly of claim 13 wherein at least one of said first, second, third and fourth pad is configured to polyaxially rotate with respect to its respective plate within a recess of the respective plate.

29. A plate assembly for attachment to a bone surface, comprising:
- a first plate comprising a first obverse side and a first reverse side opposite the first obverse side, said first plate comprising a first pad and a second pad, said pad including a plurality of protrusions configured to contact a bone surface, said first and second pads of said first plate configured to allow the pads to pivot about at least one axis relative to the first plate;
- a second plate comprising a second obverse side and a second reverse side opposite the second obverse side, said second plate comprising a third pad and a fourth pad, each pad including a plurality of protrusions configured to contact a bone surface, said third and fourth pads of said second plate configured to allow the third and fourth pads to pivot about at least one axis relative to the second plate, said first and second plates configured to cooperatively clamp a first and second spinous process wherein said first pad of said first plate and said third pad of said second plate contact a first spinous process and said second pad of said first plate and said fourth pad of said second plate contact a second spinous process; and
- a locking mechanism coupling the first plate to the second plate so that the first obverse side faces the second obverse side, said locking mechanism configured to extend longitudinally between the first obverse side of the first plate and the second obverse side of the second plate in the gap formed between the first and second spinous processes;
- wherein the plate assembly has an unlocked configuration and a locked configuration;
- wherein the plate assembly is configured to transition from the unlocked configuration to the locked configuration in response to a compression force exerted medially on the first and second plates toward the bone surface, said compression force urging the first obverse side toward the second obverse side and providing an interference lock.

30. The plate assembly of claim 29, comprising:
- an initial configuration, wherein the at least one of said first, second, third and fourth pads freely rotates relative to the plate; and
- a final configuration, wherein the at least one of said first, second, third and fourth pads is locked to the plate.

31. The plate assembly of claim 30, comprising:
- at least one spacer, wherein, in the initial configuration, the at least spacer prevents unintentional locking of the at least one of said first, second, third and fourth pads to the plate; wherein, in the final configuration, the spacer permits intentional locking of the at least one of said first, second, third and fourth pads to the plate.

32. The plate assembly of claim 31, wherein the spacer comprises a flange on the at least one of said first, second, third and fourth pads.

\* \* \* \* \*